United States Patent
St. John et al.

(10) Patent No.: US 12,410,480 B2
(45) Date of Patent: *Sep. 9, 2025

(54) METHODS AND SYSTEMS FOR DETECTING COLORECTAL CANCER VIA NUCLEIC ACID METHYLATION ANALYSIS

(71) Applicant: Freenome Holdings, Inc., South San Francisco, CA (US)

(72) Inventors: John St. John, Brisbane, CA (US); Steven Kothen-Hill, Millbrae, CA (US); Rui Yang, Burlingame, CA (US); Adam Drake, Pacifica, CA (US)

(73) Assignee: Freenome Holdings, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/163,138

(22) Filed: Feb. 1, 2023

(65) Prior Publication Data

US 2023/0220492 A1    Jul. 13, 2023

Related U.S. Application Data

(63) Continuation of application No. 17/954,576, filed on Sep. 28, 2022, which is a continuation of application No. PCT/US2021/024604, filed on Mar. 29, 2021.

(60) Provisional application No. 63/002,878, filed on Mar. 31, 2020.

(51) Int. Cl.
| | |
|---|---|
| *C12Q 1/6886* | (2018.01) |
| *C12Q 1/6806* | (2018.01) |
| *C12Q 1/6869* | (2018.01) |
| *G16B 20/10* | (2019.01) |
| *G16B 40/20* | (2019.01) |

(52) U.S. Cl.
CPC .......... *C12Q 1/6886* (2013.01); *G16B 20/10* (2019.02); *G16B 40/20* (2019.02); *C12Q 1/6806* (2013.01); *C12Q 1/6869* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 5,786,146 A | 7/1998 | Herman et al. | |
| 7,270,960 B2 | 9/2007 | Hellstrom et al. | |
| 7,727,720 B2 | 6/2010 | Dhallan | |
| 7,754,429 B2 | 7/2010 | Rigatti et al. | |
| 8,168,385 B2 | 5/2012 | Brenner | |
| 8,318,433 B2 | 11/2012 | Brenner | |
| 9,040,239 B1 | 5/2015 | Zheng et al. | |
| 9,080,210 B2 | 7/2015 | Van Eijk et al. | |
| 9,447,452 B2 | 9/2016 | Rao et al. | |
| 10,337,053 B2 | 7/2019 | Rao et al. | |
| 10,443,091 B2 | 10/2019 | Rao et al. | |
| 10,533,213 B2 | 1/2020 | Rao et al. | |
| 10,731,204 B2 | 8/2020 | Rao et al. | |
| 10,767,216 B2 | 9/2020 | Rao et al. | |
| 10,774,373 B2 | 9/2020 | Rao et al. | |
| 10,978,175 B2 | 4/2021 | Van Eijk et al. | |
| 11,072,818 B2 | 7/2021 | Rao et al. | |
| 11,208,683 B2 | 12/2021 | Rao et al. | |
| 11,514,289 B1 | 11/2022 | Otte et al. | |
| 11,681,953 B2 | 6/2023 | Drake et al. | |
| 11,781,959 B2 | 10/2023 | Delubac | |
| 11,847,532 B2 | 12/2023 | Drake et al. | |
| 2008/0194413 A1 | 8/2008 | Albert | |
| 2008/0194414 A1 | 8/2008 | Albert et al. | |
| 2009/0221438 A1 | 9/2009 | Kitzman et al. | |
| 2010/0131286 A1 | 5/2010 | Houlgatte et al. | |
| 2010/0151471 A1 | 6/2010 | Faham et al. | |

(Continued)

FOREIGN PATENT DOCUMENTS

| | | |
|---|---|---|
| CN | 105143465 A | 12/2015 |
| EP | 3152333 B1 | 9/2019 |

(Continued)

OTHER PUBLICATIONS

Li et al. (Clinical Chemistry (2019) vol. 65:7; pp. 916-926).*
Prescott et al. (PLoS Genetics (2014) vol. 11:19 pages).*
Klett et al. (Epigenetics (2018) vol. 13:386-397).*
Yagi et al. [Clin. Cancer Res., 16(1); 21-33; 2010].*
Li et al. (Bioinformatics (2002) vol. 18(11) 1427-1431).*
Asmus et al. Simultaneous Targeted Methylation Sequencing (sTM-Seq). Curr Protoc Hum Genet 101(1):e81, pp. 1-19 doi:10.1002/cphg.81 (2019).
Booth et al. Quantitative Sequencing of 5-Methylcytosine and 5-Hydroxymethylcytosine at Single-Base Resolution. Science 336(6083):934-937 (2012).
Fay et al. Confidence intervals of the Mann-Whitney parameter that are compatible with the Wilcoxon-Mann-Whitney test. Stat Med 37(27):3991-4006 doi:10.1002/sim.7890 (2018).

(Continued)

*Primary Examiner* — Lori A. Clow
(74) *Attorney, Agent, or Firm* — WILSON SONSINI GOODRICH & ROSATI

(57) ABSTRACT

The present disclosure provides methods and systems for screening or detecting a colorectal cancer or following colorectal disease progression that may be applied to cell-free nucleic acids such as cell-free DNA. The method may use detection of methylation signals within a single sequencing read in identified genomic regions as input features to train a machine learning model and generate a classifier useful for stratifying populations of individuals. The method may comprise extracting DNA from a cell-free sample obtained from a subject, converting the DNA for methylation sequencing, generating sequencing reads, and detecting colon proliferative cell disorder-associated signals in the sequencing information and training a machine learning model to provide a discriminator capable of distinguishing groups in a subject population such as healthy, cancer or distinguishing disease subtype or stage. The method may be used for, e.g., predicting, prognosticating, and/or monitoring response to treatment, tumor load, relapse, or colorectal cancer development.

13 Claims, 8 Drawing Sheets

(56) References Cited

U.S. PATENT DOCUMENTS

| | | |
|---|---|---|
| 2013/0022974 A1 | 1/2013 | Chinnaiyan et al. |
| 2014/0365243 A1 | 12/2014 | Varadan et al. |
| 2016/0040246 A1 | 2/2016 | Ahlquist et al. |
| 2017/0277844 A1 | 9/2017 | Apte et al. |
| 2018/0102187 A1 | 4/2018 | Apte et al. |
| 2018/0119137 A1 | 5/2018 | Matsuguchi et al. |
| 2020/0232894 A1 | 7/2020 | Delubac |
| 2021/0010076 A1 | 1/2021 | Delubac et al. |
| 2021/0057046 A1 | 2/2021 | Liu et al. |
| 2021/0174958 A1 | 6/2021 | Drake et al. |
| 2021/0210205 A1 | 7/2021 | Drake et al. |
| 2021/0230684 A1 | 7/2021 | Ariazi et al. |
| 2021/0272653 A1 | 9/2021 | Ulz et al. |
| 2023/0101485 A1 | 3/2023 | St. John et al. |
| 2023/0220492 A1 | 7/2023 | St. John et al. |

FOREIGN PATENT DOCUMENTS

| | | |
|---|---|---|
| WO | WO-2016115530 A1 | 7/2016 |
| WO | WO-2016119190 A1 | 8/2016 |
| WO | WO2019060716 | 3/2019 |
| WO | WO-2019071161 A1 | 4/2019 |
| WO | WO-2019100024 A1 | 5/2019 |
| WO | WO-2019147663 A1 | 8/2019 |
| WO | WO-2019191649 A1 | 10/2019 |
| WO | WO-2019195268 A2 | 10/2019 |
| WO | WO-2019200410 A1 | 10/2019 |
| WO | WO-2020076772 A1 | 4/2020 |
| WO | WO-2020243609 A1 | 12/2020 |
| WO | WO-2021202351 A1 | 10/2021 |
| WO | WO-2021222220 A2 | 11/2021 |
| WO | WO-2022076237 A1 | 4/2022 |
| WO | WO-2022140116 A1 | 6/2022 |
| WO | WO-2022204358 A1 | 9/2022 |
| WO | WO-2022261192 A1 | 12/2022 |
| WO | WO-2023003851 A1 | 1/2023 |
| WO | WO-2023147472 A1 | 8/2023 |
| WO | WO-2023183468 A2 | 9/2023 |
| WO | WO2023235878 A2 | 12/2023 |
| WO | WO2023244983 A1 | 12/2023 |
| WO | WO2023250441 A2 | 12/2023 |

OTHER PUBLICATIONS

Friedland et al. Development and Clinical Validation of a blood test for early detection of colorectal adenomas and cancer. Abstract 32305, Poster ASCO GI Meeting [1-1] (2021).

Frommer et al. A genomic sequencing protocol that yields a positive display of 5-methylcytosine residues in individual DNA strands. PNAS USA 89:1827-1831 (1992).

Geneva: World Health Organization: WHO list of priority medical devices for cancer management, WHO Medical device technical series. ISBN: 978-92-4-156546-2, License: CC BY-NC-SA 3.0 IGO, pp. 1-252 (2017).

Golub et al. Molecular classification of cancer: Class discovery and class prediction by gene expression monitoring, Science, American Association for the Advancement of Science, 286:5439 (Oct. 15, 1999), pp. 531-537.

Herman, J.G., et al. Methylation-Specific PCR: A Novel PCR Assay for Methylation Status of CpG Islands. Proceedings of the National Academy of Science USA 93:9821-9826, Sep. 1996.

Kourou et al. Machine learning applications in cancer prognosis and prediction. Comput Struct Biotechnol J.13:8-17 (2014).

Liu et al. An individualized predictor of health and disease using paired reference and target samples. BMC Bioinformatics 17:47 [1-15] (2016).

Liu et al. Bisulfite-Free Direct Detection of 5-Methylcytosine and 5-Hydroxymethylcytosine at Base Resolution. Nature Biotechnology 37(4):424-429 (2019).

Manghnani et al. METCC: METric learning for Confounder Control Making distance matter in high dimensional biological analysis. arXiv:1812.03188v1 [cs.LG] [1-10] (2018), 10 pages.

PCT/US2021/024604 International Search Report and Written Opinion dated Jul. 13, 2021.

Schutsky et al. Nondestructive, Base-Resolution Sequencing of 5-Hydroxymethylcytosine Using a DNA Deaminase. Nature Biotechnology 36(11):1083-1090 (2018).

Singh, et al. Gene expression correlates of clinical prostate cancer behavior. Cancer Cell. vol. 1, pp. 203-209 (2002).

Wan et al. Machine learning enables detection of early-stage colorectal cancer by whole-genome sequencing of plasma cell-free DNA. bioRxiv prePrint URL:https://doi.org/10.1101/478065 [1-22] (2018).

Wolpin et al. Systemic treatment of colorectal cancer. Gastroenterology 134(5):1296-1310 doi:10.1053/j.gastro.2008.02.098 (2008).

Yu et al. Tet-assisted bisulfite sequencing of 5-hydroxymethylcytosine. Nat Protoc. 7(12):2159-2170 doi:10.1038/nprot.2012.137 (2012).

Zhang et al. Tet-mediated covalent labelling of 5-methylcytosine for its genome-wide detection and sequencing, Nat Commun. 2013;4:1517, 10 pages.

CN202180039398.8 Office Action with Search Report dated Oct. 25, 2024, and a partial English translation.

PCT/US2022/024604 International Preliminary Report on Patentability dated Sep. 29, 2022.

EP21780407.9 Extended European Search Report dated Jun. 6, 2024.

* cited by examiner

METHODS AND SYSTEMS FOR DETECTING COLORECTAL CANCER VIA NUCLEIC ACID METHYLATION ANALYSIS

CROSS-REFERENCE TO RELATED APPLICATIONS

This application is a continuation of U.S. Utility application Ser. No. 17/954,576, filed Sep. 28, 2022, which is a continuation of International Application No. PCT/US2021/024604, filed Mar. 29, 2021, which claims the benefit of U.S. Provisional Patent Application No. 63/002,878, filed Mar. 31, 2020, the contents of each of which are hereby incorporated by reference in its entirety.

BACKGROUND

The present disclosure relates generally to cancer detection and disease monitoring. More particularly, the field relates to cancer-related DNA methylation detection and disease monitoring in early-stage colorectal cancer (CRC). Cancer screening and monitoring may help to improve outcomes over the past few decades because early detection leads to a better outcome as the cancer may be eliminated before it has spread. In the case of CRC, for instance, the use of colonoscopy may play a role in improving early diagnosis. Unfortunately, there may be challenges that arise due to patient compliance with screening not being adequate at recommended regularity.

A primary issue for any screening tool may be the compromise between false positive and false negative results (or specificity and sensitivity) which lead to unnecessary investigations in the former case, and ineffectiveness in the latter case. An ideal test may be one that has a high Positive Predictive Value (PPV), minimizing unnecessary investigations but detecting the vast majority of cancers. Another key factor may be what is called "detection sensitivity", to distinguish it from test sensitivity, and that is the lower limits of detection in terms of the size of the tumor. Unfortunately, waiting for a tumor to grow to a size large enough to release circulating tumor markers at levels necessary for detection may contradict the requirement for early detection in order to treat a tumor as stages where treatments are most effective. Hence, there is a need for effective blood-based screens for early-stage CRC based on circulating analytes.

The detection of circulating tumor DNA is increasingly acknowledged as a viable "liquid biopsy" allowing for the detection and informative investigation of tumors in a non-invasive manner. In some cases, using the identification of tumor specific mutations, these techniques have been applied to colon, breast and prostate cancers. Due to the high background of normal (e.g., non-tumor-derived) DNA present in the circulation, these techniques may be limited in sensitivity.

The detection of tumor-specific methylation in the blood may offer distinct advantages over the detection of mutations. A number of single or multiple methylation biomarkers may be assessed in cancers including lung, colon, and breast. These may suffer from low sensitivities as they may be insufficiently prevalent in the tumors.

There remains a need for more sensitive and specific screening tools for detecting early-stage or low tumor-burden colorectal cancer tumor signals in relapse and primary screening in at risk populations.

SUMMARY

The present disclosure provides methods and systems directed to methylation-profiling of genes associated with colorectal cancer detection and disease progression.

In an aspect, the present disclosure provides a methylation signature panel characteristic of a colon cell proliferative disorder comprising: one or more methylated genomic regions selected from the group consisting of Table 11, wherein the one or more regions are more methylated in a biological sample from an individual having a colon cell proliferative disorder or colon cell proliferative disorder subtypes, and are less methylated in normal tissues and normal blood cells in an individual not having a colon cell proliferative disorder.

In some embodiments, the biological sample is a nucleic acid, DNA, ribonucleic acid (RNA), or cell-free nucleic acid (e.g., cfDNA or cfRNA).

In some embodiments, the genomic region is a non-coding region, a coding region, or a non-transcribed or regulator region.

In some embodiments, the signature panel comprises increased methylation in two or more genomic regions selected from the group consisting of Table 11.

In some embodiments, the biological sample obtained from the subject is selected from the group consisting of cell-free DNA, cell-free RNA, body fluids, stool, colonic effluent, urine, blood plasma, blood serum, whole blood, isolated blood cells, cells isolated from the blood, and combinations thereof.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

In some embodiments, the colon cell proliferative disorder is selected from the group consisting of stage 1 colorectal cancer, stage 2 colorectal cancer, stage 3 colorectal cancer, or stage 4 colorectal cancer.

In some embodiments, the signature panel comprises two or more methylated genomic regions in Tables 1-11, three or more methylated genomic regions in Tables 1-11, four or more methylated genomic regions in Tables 1-11, five or more methylated genomic regions in Tables 1-11, six or more methylated genomic regions in Tables 1-11, seven or more methylated genomic regions in Tables 1-11, eight or more methylated genomic regions in Tables 1-11, nine or more methylated genomic regions in Tables 1-11, ten or more methylated genomic regions in Tables 1-11, eleven or more methylated genomic regions in Tables 1-11, twelve or more methylated genomic regions in Tables 1-11, or thirteen or more methylated genomic regions in Tables 1-11.

In some embodiments, the signature panel comprises genomic regions methylated in colorectal cancer comprising methylated regions in one or more genomic regions selected from the group consisting of ITGA4, EMBP1, TMEM163, SFMBT2, ELMO, and ZNF543.

In some embodiments, the regions methylated in colorectal cancer comprise methylated regions in both ITGA4 and EMBP1 genomic regions.

In some embodiments, the regions methylated in colorectal cancer comprise methylated regions in one or more genomic regions selected from the group consisting of ITGA4, EMBP1, TMEM163, SFMBT2, ELMO, ZNF543, CHST10, CCNA1, BEND4, KRBA1, S1PR1, and PPP1R16B.

In some embodiments, the signature panel comprises methylated genomic regions selected from the group consisting of Table 1, Table 2, Table 3, Table 4, Table 5, Table 6, Table 7, Table 8, Table 9, Table 10, and Table 11.

In another aspect, the present disclosure provides a methylation signature panel characteristic of a colon cell proliferative disorder comprising: two or more methylated genomic regions in Tables 1-11, wherein the two or more regions are more methylated in a biological sample from an individual having a colon cell proliferative disorder or colon cell proliferative disorder subtypes, and are less methylated in normal tissues and normal blood cells in an individual not having a colon cell proliferative disorder.

In some embodiments, the biological sample is a nucleic acid, DNA, ribonucleic acid (RNA), or cell-free nucleic acid (cfDNA or cfRNA).

In some embodiments, the genomic region is a non-coding region, a coding region, or a non-transcribed or regulator region.

In some embodiments, the signature panel comprises increased methylation in 6 or more, or 12 or more genomic regions in Tables 1-11.

In some embodiments, the biological sample obtained from the subject is selected from the group consisting of cell-free DNA, cell-free RNA, body fluids, stool, colonic effluent, urine, blood plasma, blood serum, whole blood, isolated blood cells, cells isolated from the blood, and combinations thereof.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

In some embodiments, the colon cell proliferative disorder is selected from the group consisting of stage 1 colorectal cancer, stage 2 colorectal cancer, stage 3 colorectal cancer, or stage 4 colorectal cancer.

In some embodiments, the signature panel comprises three or more methylated genomic regions in Tables 1-11, four or more methylated genomic regions in Tables 1-11, five or more methylated genomic regions in Tables 1-11, six or more methylated genomic regions in Tables 1-11, seven or more methylated genomic regions in Tables 1-11, eight or more methylated genomic regions in Tables 1-11, nine or more methylated genomic regions in Tables 1-11, ten or more methylated genomic regions in Tables 1-11, eleven or more methylated genomic regions in Tables 1-11, twelve or more methylated genomic regions in Tables 1-11, or thirteen or more methylated genomic regions in Tables 1-11.

In some embodiments, the signature panel comprises genomic regions methylated in colorectal cancer comprising methylated regions in one or more genomic regions selected from the group consisting of ITGA4, EMBP1, TMEM163, SFMBT2, ELMO, and ZNF543.

In some embodiments, the regions methylated in colorectal cancer comprise methylated regions in both ITGA4 and EMBP1 genomic regions.

In some embodiments, the regions methylated in colorectal cancer comprise methylated regions in one or more genomic regions selected from the group consisting of ITGA4, EMBP1, TMEM163, SFMBT2, ELMO, ZNF543, CHST10, CCNA1, BEND4, KRBA1, S1PR1, and PPP1R16B.

In some embodiments, the signature panel comprises methylated regions selected from the group consisting of Table 1, Table 2, Table 3, Table 4, Table 5, Table 6, Table 7, Table 8, Table 9, Table 10, and Table 11.

In another aspect, the present disclosure provides a classifier (e.g., a machine learning classifier) capable of distinguishing a population of healthy individuals from individuals with colon cell proliferative disorder comprising: a) sets of measured values representative of differentially-methylated genomic regions where the measured values are obtained from methylation sequencing data from healthy subjects and subjects having a colon cell proliferative disorder; b) wherein the measured values are used to generate a set of features corresponding to properties of the differentially-methylated genomic regions and where the features are inputted to a machine learning or statistical model; and c) wherein the model provides a feature vector useful as a classifier capable of distinguishing a population of healthy individuals from individuals having a colon cell proliferative disorder.

In some embodiments, the sets of measured values describe characteristics of the methylated regions selected from the group consisting of: base wise methylation percent for CpG, CHG, CHH, the count or rate of observing fragments with different counts or rates of methylated CpGs in a region, conversion efficiency (100-Mean methylation percent for CHH), hypomethylated blocks, methylation levels (global mean methylation for CPG, CHH, CHG, fragment length, fragment midpoint, and methylation levels in one or more genomic regions such as chrM, LINE1, or ALU), number of methylated CpGs per fragment, fraction of CpG methylation to total CpG per fragment, fraction of CpG methylation to total CpG per region, fraction of CpG methylation to total CpG in panel, dinucleotide coverage (normalized coverage of dinucleotide), evenness of coverage (unique CpG sites at 1× and 10× mean genomic coverage (for S4 runs), mean CpG coverage (depth) globally, and mean coverage at CpG islands, CGI shelves, and CGI shores.

In some embodiments, the machine learning model comprising the classifier is loaded into a memory of a computer system, the machine learning model trained using training vectors obtained from training biological samples, a first subset of the training biological samples identified as having a colon cell proliferative disorder and a second subset of the training biological samples identified as not having a colon cell proliferative disorder.

In some embodiments, the classifier is provided in a system for detecting a colon cell proliferative disorder comprising: a) a computer-readable medium comprising a classifier operable to classify subjects as having the colon cell proliferative disorder or not having the colon cell proliferative disorder based on a methylation signature panel; and b) one or more processors for executing instructions stored on the computer-readable medium.

In some embodiments, the system comprises a classification circuit that is configured as a machine learning classifier selected from the group consisting of a deep learning classifier, a neural network classifier, a linear discriminant analysis (LDA) classifier, a quadratic discriminant analysis (QDA) classifier, a support vector machine (SVM)

classifier, a random forest (RF) classifier, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and principal component analysis classifier.

In some embodiments, the computer-readable medium is a non-transitory computer-readable medium comprising machine-executable code that, upon execution by one or more computer processors, implements any of the methods above or elsewhere herein.

In some embodiments, the system comprises one or more computer processors and computer memory coupled thereto. The computer memory comprises machine-executable code that, upon execution by the one or more computer processors, implements any of the methods described herein.

In another aspect, the present disclosure provides a method for determining a methylation profile of a cell-free deoxyribonucleic acid (cfDNA) sample from an individual comprising: a) providing conditions capable of converting unmethylated cytosines to uracils in nucleic acid molecules of the cfDNA sample to produce a plurality of converted nucleic acids; b) contacting the plurality of converted nucleic acids with nucleic acid probes complementary to a pre-identified methylation signature panel of at least two differentially methylated regions selected from the group consisting of Tables 1-11 to enrich for sequences corresponding to the signature panel; c) determining nucleic acid sequences of the plurality of converted nucleic acid molecules; and d) aligning the nucleic acid sequences of the plurality of converted nucleic acid molecules to a reference nucleic acid sequence, thereby determining the methylation profile of the individual.

In some embodiments, a nucleic acid sequencing library is prepared before the amplification. In some embodiments, the method further comprises amplifying the plurality of converted nucleic acids. In some embodiments, the amplifying comprises polymerase chain reaction (PCR). In some embodiments, the method further comprises determining the nucleic acid sequences of the converted nucleic acid molecules at a depth of greater than 1000×, greater than 2000×, greater than 3000×, greater than 4000×, or greater than 5000×. In some embodiments, the reference nucleic acid sequence is at least a portion of a human reference genome. In some embodiments, the human reference genome is hg18.

In some embodiments, the methylation profile is associated with a colon cell proliferative disorder and provides classification of a subject as having a colon cell proliferative disorder.

In some embodiments, a nucleic acid adapter comprising a unique molecular identifier is ligated to unconverted nucleic acids in a cfDNA sample before a).

In some embodiments, the nucleic acid molecules are subjected to cytosine-to-uracil conversion conditions using chemical methods, enzymatic methods, or a combination thereof.

In some embodiments, the cfDNA in a biological sample is treated with a reagent selected from the group consisting of bisulfite, hydrogen sulfite, disulfite, and combinations thereof.

In some embodiments, the biological sample obtained from the subject is selected from the group consisting of cell-free DNA, cell-free RNA, body fluids, stool, colonic effluent, urine, blood plasma, blood serum, whole blood, isolated blood cells, cells isolated from the blood, and combinations thereof.

In some embodiments, the method comprises applying the measured methylation signature panel from the subject against a database of measured methylation signature panels from normal subjects, wherein the database is stored on a computer system; determining that the subject has an increased risk of having a colon cell proliferative disorder by measuring a change of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% in the methylation status of the methyl signature panel relative to methylation status from normal subjects.

In some embodiments, the pre-identified methylation signature panel includes three or more methylated genomic regions in Tables 1-11, four or more methylated genomic regions in Tables 1-11, five or more methylated genomic regions in Tables 1-11, six or more methylated genomic regions in Tables 1-11, seven or more methylated genomic regions in Tables 1-11, eight or more methylated genomic regions in Tables 1-11, nine or more methylated genomic regions in Tables 1-11, ten or more methylated genomic regions in Tables 1-11, eleven or more methylated genomic regions in Tables 1-11, twelve or more methylated genomic regions in Tables 1-11, or thirteen or more methylated genomic regions in Tables 1-11. In some embodiments, the pre-identified methylation signature panel includes one or more methylated genomic regions in Table 11, two or more methylated genomic regions in Table 11, or three methylated genomic regions in Table 11. In some embodiments, the methylation profile is indicative of a presence or an absence of a colon cell proliferative disorder in the individual.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

In some embodiments, the colon cell proliferative disorder is selected from the group consisting of stage 1 colorectal cancer, stage 2 colorectal cancer, stage 3 colorectal cancer, and stage 4 colorectal cancer.

In another aspect, the present disclosure provides a method for detecting a presence or an absence of a colon cell proliferative disorder in a subject, comprising: a) providing conditions capable of converting unmethylated cytosines to uracils in nucleic acid molecules of a biological sample obtained or derived from the subject to produce a plurality of converted nucleic acids; b) contacting the plurality of converted nucleic acids with nucleic acid probes complementary to a pre-identified methylation signature panel of at least two differentially methylated regions selected from the group consisting of Tables 1-11 to enrich for sequences corresponding to the signature panel; c) determining nucleic acid sequences of the plurality of converted nucleic acid molecules; d) aligning the nucleic acid sequences of the plurality of converted nucleic acid molecules to a reference nucleic acid sequence, thereby determining the methylation profile of the individual; and e) applying a trained machine learning model to the methylation profile, wherein the trained machine learning model is trained to be capable of distinguishing between healthy individuals and individuals with a colon cell proliferative disorder to provide an output value associated with presence of a colon cell proliferative disorder, thereby detecting the presence or the absence of the colon cell proliferative disorder in the subject.

In some embodiments, a nucleic acid sequencing library is prepared before the amplification. In some embodiments, the method further comprises amplifying the plurality of converted nucleic acids. In some embodiments, the amplifying comprises polymerase chain reaction (PCR). In some embodiments, the method further comprises determining the nucleic acid sequences of the converted nucleic acid molecules at a depth of greater than 1000×, greater than 2000×, greater than 3000×, greater than 4000×, or greater than 5000×. In some embodiments, the reference nucleic acid sequence is at least a portion of a human reference genome. In some embodiments, the human reference genome is hg18.

In some embodiments, the biological sample obtained from the subject is selected from the group consisting of cell-free DNA, cell-free RNA, body fluids, stool, colonic effluent, urine, blood plasma, blood serum, whole blood, isolated blood cells, cells isolated from the blood, and combinations thereof.

In some embodiments, the method comprises applying the measured methylation signature panel from the subject against a database of measured methylation signature panels from normal subjects, wherein the database is stored on a computer system; determining that the subject has an increased risk of having a colon cell proliferative disorder by measuring a change of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% in the methylation status of the methyl signature panel relative to methylation status from normal subjects.

In some embodiments, the pre-identified methylation signature panel includes three or more methylated genomic regions in Tables 1-11, four or more methylated genomic regions in Tables 1-11, five or more methylated genomic regions in Tables 1-11, six or more methylated genomic regions in Tables 1-11, seven or more methylated genomic regions in Tables 1-11, eight or more methylated genomic regions in Tables 1-11, nine or more methylated genomic regions in Tables 1-11, ten or more methylated genomic regions in Tables 1-11, eleven or more methylated genomic regions in Tables 1-11, twelve or more methylated genomic regions in Tables 1-11, or thirteen or more methylated genomic regions in Tables 1-11. In some embodiments, the pre-identified methylation signature panel includes one or more methylated genomic regions in Table 11, two or more methylated genomic regions in Table 11, or three methylated genomic regions in Table 11. In some embodiments, the methylation profile is indicative of a presence or an absence of a colon cell proliferative disorder in the individual. In some embodiments, the method further comprises administering a treatment to the individual for the colon cell proliferative disorder based on detecting the presence of the colon cell proliferative disorder in the individual.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

In some embodiments, the trained machine learning classifier is selected from the group consisting of a deep learning classifier, a neural network classifier, a linear discriminant analysis (LDA) classifier, a quadratic discriminant analysis (QDA) classifier, a support vector machine (SVM) classifier, a random forest (RF) classifier, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and a principal component analysis classifier.

In some embodiments, the colon cell proliferative disorder is selected from the group consisting of stage 1 colorectal cancer, stage 2 colorectal cancer, stage 3 colorectal cancer, and stage 4 colorectal cancer.

In another aspect, the present disclosure provides a method for monitoring minimal residual disease in a subject previously treated for disease comprising: determining a methylation profile as described herein as a baseline methylation state and repeating an analysis to determine the methylation profile at one or more pre-determined time points wherein a change from baseline indicates a change in the minimal residual disease status at baseline in the subject.

In some embodiments, the minimal residual disease is selected from the group consisting of response to treatment, tumor load, residual tumor post-surgery, relapse, secondary screen, primary screen, and cancer progression.

In another aspect, a method is provided for determining response to treatment.

In another aspect, a method is provided for monitoring tumor load.

In another aspect, a method is provided for detecting residual tumor post-surgery.

In another aspect, a method is provided for detecting relapse.

In another aspect, a method is provided for use as a secondary screen.

In another aspect, a method is provided for use as a primary screen.

In another aspect, a method is provided for monitoring cancer progression.

In some embodiments, the dataset is indicative of the presence or susceptibility of the colorectal cancer at a sensitivity of at least about 80%. In some embodiments, the dataset is indicative of the presence or susceptibility of the colorectal cancer at a sensitivity of at least about 90%. In some embodiments, the dataset is indicative of the presence or susceptibility of the colorectal cancer at a sensitivity of at least about 95%. In some embodiments, the dataset is indicative of the presence or susceptibility of the colorectal cancer at a positive predictive value (PPV) of at least about 70%. In some embodiments, the dataset is indicative of the presence or susceptibility of the colorectal cancer at a positive predictive value (PPV) of at least about 80%. In some embodiments, the dataset is indicative of the presence or susceptibility of the colorectal cancer at a positive predictive value (PPV) of at least about 90%. In some embodiments, the dataset is indicative of the presence or susceptibility of the colorectal cancer at a positive predictive value (PPV) of at least about 95%. In some embodiments, the dataset is indicative of the presence or susceptibility of the colorectal cancer at a positive predictive value (PPV) of at least about 99%. In some embodiments, the dataset is indicative of the presence or susceptibility of the colorectal cancer at a negative predictive value (NPV) of at least about 80%. In some embodiments, the dataset is indicative of the presence or susceptibility of the colorectal cancer at a negative predictive value (NPV) of at least about 90%. In some embodiments, the dataset is indicative of the presence or susceptibility of the colorectal cancer at a negative predictive value (NPV) of at least about 95%. In some embodiments, the dataset is indicative of the presence or susceptibility of the colorectal cancer at a negative predictive value (NPV) of at least about 99%. In some embodiments, the trained algorithm determines the presence or susceptibility of the colorectal cancer of the subject with an Area Under Curve (AUC) of at least about 0.90. In some embodiments, the trained algorithm determines the presence or susceptibility of the colorectal cancer of the subject with an Area Under Curve (AUC) of at least about 0.95. In some embodiments, the trained algorithm determines the presence or susceptibility of the colorectal cancer of the subject with an Area Under Curve (AUC) of at least about 0.99.

In some embodiments, the method further comprises presenting a report a graphical user interface of an electronic device of a user. In some embodiments, the user is the subject, individual or patient.

In some embodiments, the method further comprises determining a likelihood of the determination of a presence or susceptibility of colorectal cancer in the subject, individual, or patient. For example, the likelihood may be a probability value between 0% and 100%.

In some embodiments, the trained algorithm (e.g., machine learning model or classifier) comprises a supervised machine learning algorithm. In some embodiments, the supervised machine learning algorithm comprises a deep learning algorithm, a support vector machine (SVM), a neural network, or a Random Forest.

In some embodiments, the method further comprises providing said subject with a therapeutic intervention based at least in part on the methylation profile or analysis, such as a therapeutic intervention to treat a patient with colorectal cancer (e.g., chemotherapy, radiotherapy, immunotherapy, or surgery).

In some embodiments, the method further comprises monitoring the presence or susceptibility of the colorectal cancer, wherein said monitoring comprises assessing the presence or susceptibility of the colorectal cancer of said subject at a plurality of time points, wherein the assessing is based at least on the presence or susceptibility of the colorectal cancer determined each of the plurality of time points.

In some embodiments, a difference in the assessment of the presence or susceptibility of the colorectal cancer of the subject among the plurality of time points is indicative of one or more clinical indications selected from the group consisting of: (i) a diagnosis of the presence or susceptibility of the colorectal cancer of the subject, (ii) a prognosis of the presence or susceptibility of the colorectal cancer of the subject, and (iii) an efficacy or non-efficacy of a course of treatment for treating the presence or susceptibility of the colorectal cancer of the subject.

In some embodiments, the method further comprises stratifying the colorectal cancer of the subject by using the trained algorithm to determine a sub-type of the colorectal cancer of the subject from among a plurality of distinct subtypes or stages of colorectal cancer.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Examples of the present disclosure will now be described, by way of example only, with reference to the attached Figures. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-3F show the ROC results showing the ability of these differentially methylated regions (DMRs) to detect CRC and to differentiate early-stage cancer, including patients with stage 1 (FIG. 3A), stage 2 (FIG. 3B), stage 3 (FIG. 3C), stage 4 (FIG. 3D), missing stage (FIG. 3E), and all samples (FIG. 3F).

DETAILED DESCRIPTION

Figure 1:
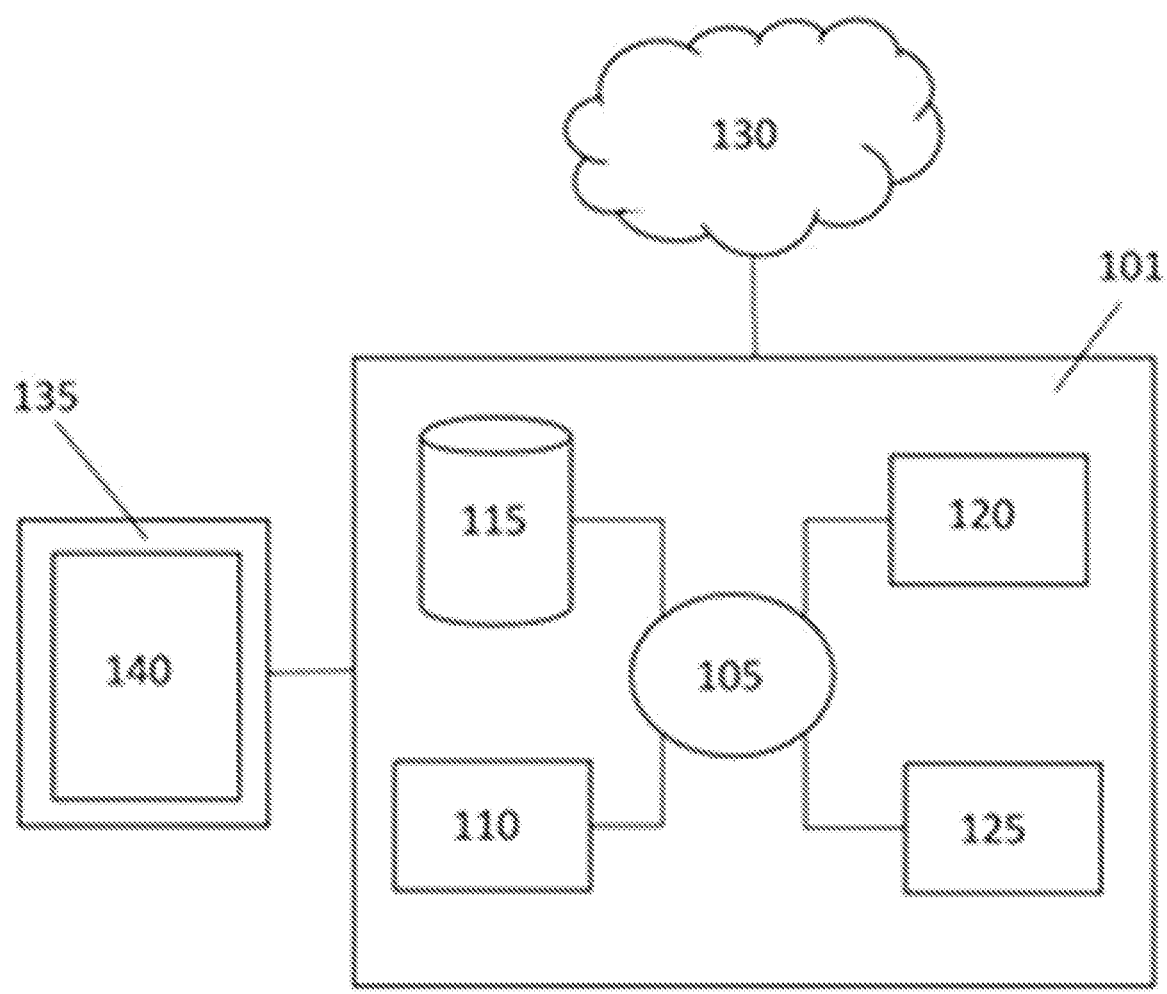
FIG. 1 provides a schematic of a computer system that is programmed or otherwise configured with the machine learning models and classifiers in order to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure relates generally to cancer detection and disease monitoring. More particularly, the field relates to cancer-related DNA methylation detection and disease monitoring in early-stage colorectal cancer. Cancer screening and monitoring may help to improve outcomes over the past few decades because early detection leads to a better outcome as the cancer may be eliminated before it has spread. In the case of colorectal cancer, for instance, the use of colonoscopy may play a role in improving early diagnosis. Unfortunately, there may be challenges that arise due to patient compliance with screening not being adequate at recommended regularity.

A primary issue for any screening tool may be the compromise between false positive and false negative results (or specificity and sensitivity) which lead to unnecessary investigations in the former case, and ineffectiveness in the latter case. An ideal test may be one that has a high Positive Predictive Value (PPV), minimizing unnecessary investigations but detecting the vast majority of cancers. Another key factor may be what is called "detection sensitivity", to distinguish it from test sensitivity, and that is the lower limits of detection in terms of the size of the tumor. Unfortunately, waiting for a tumor to grow to a size large enough to release circulating tumor markers at levels necessary for detection may contradict the requirement for early detection in order to treat a tumor as stages where treatments are most effective. Hence, there is a need for effective blood-based screens for early-stage colorectal cancer based on circulating analytes.

The detection of circulating tumor DNA is increasingly acknowledged as a viable "liquid biopsy" allowing for the detection and informative investigation of tumors in a non-invasive manner. In some cases, using the identification of tumor specific mutations, these techniques have been applied to colon, breast and prostate cancers. Due to the high background of normal (e.g., non-tumor-derived) DNA present in the circulation, these techniques may be limited in sensitivity.

The detection of tumor-specific methylation in the blood may offer distinct advantages over the detection of mutations. A number of single or multiple methylation biomarkers may be assessed in cancers including lung, colon, and breast. These may suffer from low sensitivities as they may be insufficiently prevalent in the tumors.

There remains a need for more sensitive and specific screening tools for detecting early-stage or low tumor-burden colorectal cancer tumor signals in relapse and primary screening in at risk populations.

The present disclosure provides methods and systems directed to methylation-profiling of genes associated with colorectal cancer detection and disease progression.

In an aspect, the present disclosure provides methods that use a panel of methylated regions useful for the analysis of methylation within a region or gene, other aspects provide novel uses of the region, gene and the gene product as well as methods, assays and kits directed to detecting, differentiating and distinguishing colon cell proliferative disorders. The method and nucleic acids provided herein may be used for the analysis of colon cell proliferative disorders taken from the group consisting of adenocarcinomas, adenomas, polyps, squamous cell cancers, carcinoid tumors, sarcomas, and lymphomas.

In some embodiments, the method comprises the use of one or more genes selected from the group consisting of methylated regions as markers for the differentiation, detection, and distinguishing of colon cell proliferative disorders. The use of the gene may be enabled by means of analysis of the methylation status of one or more genes selected from the methylated regions described here and their promoter or regulatory elements.

Methods and systems of the present disclosure may comprise analysis of the methylation state of the CpG dinucleotides within one or more of the genomic sequences according to methylated regions described here and sequences complementary thereto.

I. Definitions

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has cancer or is suspected of having cancer. The subject may be displaying a symptom(s) indicative of a health or physiological state or condition of the subject, such as a cancer or other disease, disorder, or condition of the subject. As an alternative, the subject can be asymptomatic with respect to such health or physiological state or condition.

As used herein, the term "sample," generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free fetal DNA (cffDNA), plasma, serum, urine, saliva, amniotic fluid, and derivatives thereof. Cell-free biological samples may be obtained or derived from subjects using an ethylenediaminetetraacetic acid (EDTA) collection tube, a cell-free RNA collection tube (e.g., Streck®), or a cell-free DNA collection tube (e.g., Streck®). Cell-free biological samples may be derived from whole blood samples by fractionation (e.g., centrifugation into a cellular component and a cell-free component). Biological samples or derivatives thereof may contain cells. For example, a biological sample may be a blood sample or a derivative thereof (e.g., blood collected by a collection tube or blood drops).

As used herein, the term "nucleic acid" generally refers to a polymeric form of nucleotides of any length, either deoxyribonucleotides (dNTPs) or ribonucleotides (rNTPs), or analogs thereof. Nucleic acids may have any three-dimensional structure, and may perform any function, known or unknown. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the terms "amplifying" and "amplification" generally refer to increasing the size or quantity of a nucleic acid molecule. The nucleic acid molecule may be single-stranded or double-stranded. Amplification may include generating one or more copies or "amplified product" of the nucleic acid molecule. Amplification may be performed, for example, by extension (e.g., primer extension) or ligation. Amplification may include performing a primer extension reaction to generate a strand complementary to a single-stranded nucleic acid molecule, and in some cases generate one or more copies of the strand and/or the single-stranded nucleic acid molecule. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase The term "cell-free nucleic acid (cfNA)", as used herein, generally refers to nucleic acids (such as cell-free RNA ("cfRNA") or cell-free DNA ("cfDNA")) in a biological sample that are not contained in a cell. cfDNA may circulate freely in in a bodily fluid, such as in the bloodstream.

The term "cell-free sample", as used herein, generally refers to a biological sample that is substantially devoid of intact cells. This may be derived from a biological sample that is itself substantially devoid of cells or may be derived from a sample from which cells have been removed. Examples of cell-free samples include those derived from blood, such as serum or plasma; urine; or samples derived from other sources, such as semen, sputum, feces, ductal exudate, lymph, or recovered lavage.

The term "circulating tumor DNA", as used herein, generally refers to cfDNA originating from a tumor.

The term "genomic region", as used herein, generally refers to identified regions of nucleic acid that are identified by their location in the chromosome. In some examples, the genomic regions are referred to by a gene name and encompass coding and non-coding regions associated with that physical region of nucleic acid. As used herein, a gene comprises coding regions (exons), non-coding regions (introns), transcriptional control or other regulatory regions, and promoters. In another example, the genomic region may incorporate an intron or exon or an intron/exon boundary within a named gene.

The term "CpG islands", as used herein, generally refers to a contiguous region of genomic DNA that satisfies the criteria of: (1) having a frequency of CpG dinucleotides corresponding to an "Observed/Expected Ratio" greater than about 0.6; and (2) having a "GC Content" greater than about 0.5. CpG islands are typically, but not always, between about 0.2 to about 3 kilobases (kb) in length having a high frequency of CpG sites. CpG islands are found at or near promoters of about 40% of mammalian genes. CpG islands are also found outside of mammalian genes. In some examples, CpG islands are found in exons, introns, promoters, enhancers, inhibitors, and transcriptional regulatory elements. CpG islands may tend to occur upstream of so-called "housekeeping genes". CpG islands may be said to have a CpG dinucleotide content of at least about 60% of what would be statistically expected. The occurrence of CpG islands at or upstream of 5' end of genes may reflect a role in the regulation of transcription, and methylation of CpG sites within the promoters of genes may lead to silencing. Silencing of tumor suppressors by methylation is, in turn, a hallmark of a number of human cancers.

The term "CpG shores", as used herein, generally refers to regions extending short distances from CpG islands in which methylation may also occur. CpG shores may be found in the region about 0 to 2 kb upstream and downstream of a CpG island.

The term "CpG shelves", as used herein, generally refers to regions extending short distances from CpG shores in which methylation may also occur. CpG shelves may generally be found in the region between about 2 kb and 4 kb upstream and downstream of a CpG island (e.g., extending a further 2 kb out from a CpG shore).

The term "colon cell proliferative disorder", as used herein, generally refers to a disorder or disease that comprises disordered or aberrant proliferation of cells in the colon or rectum. In some examples, the disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

The term "epigenetic parameters", as used herein, generally refers to cytosine methylations. Further epigenetic parameters include, for example, the acetylation of histones which, while they may not be directly analyzed using the described method, but which, in turn, correlate with the DNA methylation.

The term "genetic parameters", as used herein, generally refers to mutations and polymorphisms of genes and sequences further required for their regulation. Examples of mutations include insertions, deletions, point mutations, inversions, and polymorphisms such as SNPs (single nucleotide polymorphisms).

The term "hemi-methylation" or "hemimethylation", as used herein, generally refers to the methylation state of a palindromic CpG methylation site, where only a single cytosine in one of the two CpG dinucleotide sequences of the palindromic CpG methylation site is methylated (e.g., 5'-CCMGG-3' (top strand): 3'-GGCC-5' (bottom strand)).

The term "hypermethylation", as used herein, generally refers to the average methylation state corresponding to an increased presence of 5-mC at one or a plurality of CpG dinucleotides within a DNA sequence of a test DNA sample, relative to the amount of 5-mC found at corresponding CpG dinucleotides within a normal control DNA sample. In some embodiments, the test DNA sample is from an individual having a colon cell proliferative disorder.

The term "hypomethylation", as used herein, generally refers to the average methylation state corresponding to a decreased presence of 5-mC at one or a plurality of CpG dinucleotides within a DNA sequence of a test DNA sample, relative to the amount of 5-mC found at corresponding CpG dinucleotides within a normal control DNA sample. In some embodiments, the test DNA sample is from an individual having a colon cell proliferative disorder.

The term "methylation state" or "methylation status", as used herein, generally refers to the presence or absence of 5-methylcytosine ("5-mC") at one or a plurality of CpG dinucleotides within a DNA sequence. Methylation states at one or more particular palindromic CpG methylation sites (each having two CpG dinucleotide sequences) within a DNA sequence include "unmethylated," "fully-methylated" and "hemi-methylated."

The term "methylated cytosine", as used herein, generally refers to any methylated forms of the nucleic acid base cytosine that contains a methyl or hydroxymethyl functional group at the 5' position. Methylated cytosines are known to be regulators of gene transcription in genomic DNA. This term may include 5-methylcytosine and 5-hydroxymethyl-cytosine.

The term "methylation assay", as used herein, generally refers to any assay for determining the methylation state of one or more CpG dinucleotide sequences within a sequence of DNA.

The term "minimal residual disease" or "MRD", as used herein, generally refers to the small number of cancer cells in the body after cancer treatment. MRD testing may be performed to determine whether the cancer treatment is working and to guide further treatment plans.

The term "MSP" (methylation-specific polymerase chain reaction (PCR)), as used herein, generally refers to a methylation assay, such as that described by Herman et al. Proc. Natl. Acad. Sci. USA 93:9821-9826, 1996, and by U.S. Pat. No. 5,786,146, the contents of each of which are incorporated herein by reference.

The term "methylation converted" or "converted" nucleic acid, as used herein, generally refers to nucleic acid, such as for example DNA, that has undergone a process used to convert the DNA for methylation sequencing. Examples of conversion processes include reagent-based (such as bisulfite) conversion, enzymatic conversion, or combination conversion (such as TET-assisted pyridine borane sequencing (TAPS) conversion), where unmethylated cytosines are converted into uracil prior to PCR amplification or sequencing. The conversion process may be used in methyl sequencing methods to distinguish between methylated and unmethylated cytosine bases.

The term "region methylated in cancer", as used herein, generally refers to a segment of the genome containing methylation sites (CpG dinucleotides), methylation of which is associated with a malignant cellular state. Methylation of a region may be associated with more than one different type of cancer, or with one type of cancer specifically. Further, methylation of a region may be associated with more than one cancer subtype, or with one cancer subtype specifically.

The terms cancer "type" and "subtype", generally are used relatively herein, such that one "type" of cancer, such as breast cancer, may be "subtypes" based on e.g., stage, morphology, histology, gene expression, receptor profile, mutation profile, aggressiveness, prognosis, malignant characteristics, etc. Likewise, "type" and "subtype" may be applied at a finer level, e.g., to differentiate one histological "type" into "subtypes", e.g., defined according to mutation profile or gene expression. Cancer "stage" is also used to refer to classification of cancer types based on histological and pathological characteristics relating to disease progression.

II. Assaying Samples

The cell-free biological samples may be obtained or derived from a human subject. The cell-free biological samples may be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, cell-free RNA collection tubes, or cell-free DNA collection tubes).

The cell-free biological sample may be obtained from a subject with a cancer, from a subject that is suspected of having a cancer, or from a subject that does not have or is not suspected of having the cancer.

The cell-free biological sample may be taken before and/or after treatment of a subject with the cancer. Cell-free biological samples may be obtained from a subject during a treatment or a treatment regime. Multiple cell-free biological samples may be obtained from a subject to monitor the effects of the treatment over time. The cell-free biological sample may be taken from a subject known or suspected of having a cancer for which a definitive positive or negative diagnosis is not available via clinical tests. The sample may be taken from a subject suspected of having a cancer. The cell-free biological sample may be taken from a subject experiencing unexplained symptoms, such as fatigue, nausea, weight loss, aches and pains, weakness, or bleeding. The cell-free biological sample may be taken from a subject having explained symptoms. The cell-free biological sample may be taken from a subject at risk of developing a cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The cell-free biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, or a mixture or combination thereof. One or more such analytes (e.g., cfRNA molecules and/or cfDNA molecules) may be isolated or extracted from one or more cell-free biological samples of a subject for downstream assaying using one or more suitable assays.

After obtaining a cell-free biological sample from the subject, the cell-free biological sample may be processed to generate datasets indicative of a cancer of the subject. For example, a presence, absence, or quantitative assessment of nucleic acid molecules of the cell-free biological sample at a panel of cancer-associated genomic loci (e.g., quantitative measures of RNA transcripts or DNA at the cancer-associated genomic loci). In some embodiments, processing the cell-free biological sample obtained from the subject may comprise: (i) subjecting the cell-free biological sample to conditions that are sufficient to isolate, enrich, or extract a plurality of nucleic acid molecules; and (ii) assaying the plurality of nucleic acid molecules to generate the dataset.

In some embodiments, a plurality of nucleic acid molecules is extracted from the cell-free biological sample and subjected to sequencing to generate a plurality of sequencing reads. The nucleic acid molecules may comprise ribonucleic acid (RNA) or deoxyribonucleic acid (DNA). The nucleic acid molecules (e.g., RNA or DNA) may be extracted from the cell-free biological sample by a variety of methods, such as a FastDNA® Kit protocol from MP Biomedicals®, a QIAamp® DNA cell-free biological mini kit from Qiagen®, or a cell-free biological DNA isolation kit protocol from Norgen Biotek R. The extraction method may extract all RNA or DNA molecules from a sample. Alternatively, the extraction method may selectively extract a portion of RNA or DNA molecules from a sample. Extracted RNA molecules from a sample may be converted to DNA molecules by reverse transcription (RT).

The sequencing may be performed by any suitable sequencing methods, such as massively parallel sequencing (MPS), paired-end sequencing, high-throughput sequencing, next-generation sequencing (NGS), shotgun sequencing, single-molecule sequencing, nanopore sequencing, semiconductor sequencing, pyrosequencing, sequencing-by-synthesis (SBS), sequencing-by-ligation, sequencing-by-hybridization, and RNA-Seq® (Illumina®).

The sequencing may comprise nucleic acid amplification (e.g., of RNA or DNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., RNA or DNA) to a desired input quantity for subsequent sequencing. In some cases, the PCR may be used for global amplification of target nucleic acids. This may comprise using adapter sequences that may be first ligated to different molecules followed by PCR amplification using universal primers. PCR may be performed using any of a number of commercial kits, e.g., provided by Life Technologies®, Affymetrix®, Promega®, Qiagen®, etc. In other cases, only certain target nucleic acids within a population of nucleic acids may be amplified. Specific primers, possibly in conjunction with adapter ligation, may be used to selectively amplify certain targets for downstream sequencing. The PCR may comprise targeted amplification of one or more genomic loci, such as genomic loci associated with cancers. The sequencing may comprise use of simultaneous reverse transcription (RT) and polymerase chain reaction (PCR), such as a OneStep RT-PCR kit protocol by Qiagen®, NEB®, Thermo Fisher Scientific®, or Bio-Rad®.

RNA or DNA molecules isolated or extracted from a cell-free biological sample may be tagged, e.g., with identifiable tags, to allow for multiplexing of a plurality of samples. Any number of RNA or DNA samples may be multiplexed. For example a multiplexed reaction may contain RNA or DNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial cell-free biological samples. For example, a plurality of cell-free biological samples may be tagged with sample barcodes such that each DNA molecule may be traced back to the sample (and the subject) from which the DNA molecule originated. Such tags may be attached to RNA or DNA molecules by ligation or by PCR amplification with primers.

After subjecting the nucleic acid molecules to sequencing, suitable bioinformatics processes may be performed on the sequence reads to generate the data indicative of the presence, absence, or relative assessment of the cancer. For example, the sequence reads may be aligned to one or more reference genomes (e.g., a genome of one or more species such as a human genome, e.g., hg19). The aligned sequence reads may be quantified at one or more genomic loci to generate the datasets indicative of the cancer. For example, quantification of sequences corresponding to a plurality of genomic loci associated with cancers may generate the datasets indicative of the cancer.

The cell-free biological sample may be processed without any nucleic acid extraction. For example, the cancer may be identified or monitored in the subject by using probes configured to selectively enrich nucleic acid (e.g., RNA or DNA) molecules corresponding to the plurality of cancer-associated genomic loci. The probes may be nucleic acid primers. The probes may have sequence complementarity with nucleic acid sequences from one or more of the plurality of cancer-associated genomic loci or genomic regions. The plurality of cancer-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct cancer-associated genomic loci or genomic regions. The plurality of cancer-associated genomic loci or genomic regions may comprise one or more members (e.g., 1, 2, 3, 4, 5, 6, 7, 8, 9, 10, 11, 12, 13, 14, 15, 16, 17, 18, 19, 20, about 25, about 30, about 35, about 40, about 45, about 50, about 55, about 60, about 65, about 70, about 75, about 80, or more) selected from the group listed in Tables 1-11. The cancer-associated genomic loci or genomic regions may be associated with various stages or sub-types of cancer (e.g., colorectal cancer).

The probes may be nucleic acid molecules (e.g., RNA or DNA) having sequence complementarity with nucleic acid sequences (e.g., RNA or DNA) of the one or more genomic loci (e.g., cancer-associated genomic loci). These nucleic acid molecules may be primers or enrichment sequences. The assaying of the cell-free biological sample using probes that are selective for the one or more genomic loci (e.g., cancer-associated genomic loci) may comprise use of array hybridization (e.g., microarray-based), polymerase chain reaction (PCR), or nucleic acid sequencing (e.g., RNA sequencing or DNA sequencing). In some embodiments, DNA or RNA may be assayed by one or more of: isothermal DNA/RNA amplification methods (e.g., loop-mediated isothermal amplification (LAMP), helicase dependent amplification (HDA), rolling circle amplification (RCA), recombinase polymerase amplification (RPA)), immunoassays, electrochemical assays, surface-enhanced Raman spectroscopy (SERS), quantum dot (QD)-based assays, molecular inversion probes, droplet digital PCR (ddPCR), CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), and CRISPR-mediated analog multi-event recording apparatus (CAMERA)), and laser transmission spectroscopy (LTS).

The assay readouts may be quantified at one or more genomic loci (e.g., cancer-associated genomic loci) to generate the data indicative of the cancer. For example, quantification of array hybridization or polymerase chain reaction (PCR) corresponding to a plurality of genomic loci (e.g., cancer-associated genomic loci) may generate data indicative of the cancer. Assay readouts may comprise quantitative PCR (qPCR) values, digital PCR (dPCR) values, digital droplet PCR (ddPCR) values, fluorescence values, etc., or normalized values thereof. The assay may be a home use test configured to be performed in a home setting.

In some embodiments, multiple assays may be used to simultaneously process cell-free biological samples of a subject. For example, a first assay may be used to process a first cell-free biological sample obtained or derived from the subject to generate a first dataset indicative of the cancer; and a second assay different from the first assay may be used to process a second cell-free biological sample obtained or derived from the subject to generate a second dataset indicative of the cancer. Any or all of the first dataset and the second dataset may then be analyzed to assess the cancer of the subject. For example, a single diagnostic index or diagnosis score can be generated based on a combination of the first dataset and the second dataset. As another example, separate diagnostic indexes or diagnosis scores can be generated based on the first dataset and the second dataset.

The cell-free biological samples may be processed using a methylation-specific assay. For example, a methylation-specific assay can be used to identify a quantitative measure (e.g., indicative of a presence, absence, or relative amount) of methylation each of a plurality of cancer-associated genomic loci in a cell-free biological sample of the subject. The methylation-specific assay may be configured to process cell-free biological samples such as a blood sample or a urine sample (or derivatives thereof) of the subject. A quantitative measure (e.g., indicative of a presence, absence, or relative amount) of methylation of cancer-associated genomic loci in the cell-free biological sample may be indicative of one or more cancers. The methylation-specific assay may be used to generate datasets indicative of the quantitative measure (e.g., indicative of a presence, absence, or relative amount) of methylation of each of a plurality of cancer-associated genomic loci in the cell-free biological sample of the subject.

The methylation-specific assay may comprise, for example, one or more of: a methylation-aware sequencing (e.g., using bisulfite treatment), pyrosequencing, methylation-sensitive single-strand conformation analysis (MS-SSCA), high-resolution melting analysis (HRM), methylation-sensitive single-nucleotide primer extension (MS-SnuPE), base-specific cleavage/MALDI-TOF, microarray-based methylation assay, methylation-specific PCR, targeted bisulfite sequencing, oxidative bisulfite sequencing, mass spectroscopy-based bisulfite sequencing, or reduced representation bisulfite sequence (RRBS).

III. Signature Panels

The present disclosure provides methods and systems to analyze biological samples to obtain measurable features from a combination of hypermethylated regions in DNA in the sample that are associated with the development of colon cell proliferative disorders to identify a signature panel of regions. The features from the signature panel may be processed using a trained algorithm (e.g., a machine learning model) to create a classifier configured to stratify a population of individuals with a colon cell proliferative disorder. The methods are characterized by using one or more nucleic acids having methylated regions described in the signature panels which are contacted with a reagent or series of reagents capable of distinguishing between methylated and non-methylated CpG dinucleotides within the identified regions prior to sequencing.

The signature panels described herein generally refer to a collection of targeted regions of genomic DNA that are identified in a cell-free nucleic acid sample and display an increased methylation at cytosine bases in samples associated with a colon cell proliferative disorder. The formation of signature panels allows for a quick and specific analysis of specific methylated regions associated with colon cell proliferative disorders. The signature panel(s) as described and employed in the methods herein may be used for the improved diagnosis, prognosis, treatment selection, and monitoring (e.g., treatment monitoring) of colon cell proliferative disorders.

The signature panels and methods of the present disclosure may provide significant improvements over current approaches in addressing a need for markers or signature panels used to detect early-stage colon cell proliferative disorders from body fluid samples such as whole blood, plasma or serum. Current methods used to detect and diagnose colon cell proliferative disorders include colonoscopy, sigmoidoscopy, and fecal occult blood colon cancer. In comparison to these methods, the methods provided herein may be much less invasive than colonoscopy, and at least equally or more sensitive, than sigmoidoscopy, fecal immunochemical test (FIT), and fecal occult blood test (FOBT). Compared to the current use of these markers, methods provided herein may provide significant advantages in terms of sensitivity and specificity due to the advantageous combination of using a gene panel and highly sensitive assay techniques.

In some embodiments, the regions methylated in cancer comprise CpG islands. In some embodiments, the regions methylated in cancer comprise CpG shores. In some embodiments, the regions methylated in cancer comprise CpG shelves. In some embodiments, the regions methylated in cancer comprise CpG islands and CpG shores. In some embodiments, the regions methylated in cancer comprise CpG islands, CpG shores, and CpG shelves.

In some embodiments, the regions methylated in cancer comprise CpG islands and sequences about 0 to 4 kilobases (kb) upstream and downstream. The regions methylated in cancer may also comprise CpG islands and sequences about 0 to 3 kb upstream and downstream, about 0 to 2 kb upstream and downstream, about 0 to 1 kb upstream and downstream, about 0 to 500 base pairs (bp) upstream and downstream, about 0 to 400 bp upstream and downstream, about 0 to 300 bp upstream and downstream, about 0 to 200 bp upstream and downstream, or about 0 to 100 bp upstream and downstream.

A number of design parameters may be considered in the selection of regions hypermethylated in cancer, according to some examples. In certain examples, the methylation region is about 200 bp, about 300 bp, about 400 bp, or about 500 bp in length. Data for this selection process may be obtained from a variety of sources, such as, e.g., The Cancer Genome Atlas (TCGA) (cancergenome.nih.gov), derived by the use of, e.g., Illumina® Infinium HumanMethylation450 BeadChip for a wide range of cancers, or from other sources based on, e.g., bisulfite whole genome sequencing or other methodologies. In some embodiments, "methylation value" (which may be derived from TCGA level 3 methylation data, which is in turn derived from the beta-value, which ranges from about −0.5 to 0.5) may be used to select regions. In some embodiments, the amplification is performed with primer sets designed to amplify at least one methylation site having a methylation value of below about −0.3 in normal issue. This may be established in a plurality of normal tissue samples, such as about 4. The methylation value may be at or below about −0.1, about −0.2, about −0.3, about −0.4, about −0.5, about −0.6, about −0.7, about −0.8, about −0.9, or about −1.0.

In some embodiments, the primer sets are designed to amplify at least one methylation site having a difference between the average methylation value in the cancer and the normal tissue of greater than a predefined threshold, such as about 0.3. In some embodiments, the difference may be greater than about 0.1, about 0.2, about 0.3, about 0.4, about 0.5, about 0.6, about 0.7, about 0.8, about 0.9, or about 1.0. Proximity of other methylation sites that meet this requirement may also play a role in selecting regions, in some examples. In some embodiments, the primer sets include primer pairs amplifying at least one methylation site having at least one methylation site within about 200 bp that also has a methylation value of below about −0.3 in normal issue, and a difference between the average methylation value in the cancer and the normal tissue of greater than about 0.3.

In some examples, target regions are selected if the methylation in a region is greater than methylation in the same region in samples obtained or derived from one or more healthy individuals (e.g., individuals without cancer). Such selection may be performed manually or computationally. In certain examples, a region may be selected if it has at least about 5%, about 10%, about 15%, about 20%, about 30%, about 40%, about 50%, about 55%, about 60%, about 65%, about 70%, about 75%, about 80%, about 85%, about 90%, about 95%, about 100%, or more than about 100% more methylation than a sample from a healthy individual. In another example, a region may be selected if the number of reads mapped to the region in a disease sample at a predefined threshold methylated CpG count exceeds the same predefined threshold methylated CpG count for the same region in healthy individual samples. The methylated CpG count used as a baseline threshold in healthy samples may change for a given region, but the number of reads mapping to that region that exceeds the baseline threshold of methylated CpG count for that region in a healthy sample may indicate an important region regardless of the fluctuating threshold CpG count.

In some examples, target regions may be selected for amplification based on the number of samples in the validation set having methylation at that site. For example, a region may be selected if it is more methylated in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% of samples tested from disease individuals compared to samples from healthy individuals. For example, regions may be selected if they are methylated in at least about 75% of tumors tested, including within specific subtypes. For some validations, tumor-derived cell lines may be used for the testing.

The present disclosure further provides a method for conducting an assay in order to ascertain genetic and/or epigenetic parameters of one or more genes selected from the group consisting of the signature panels described herein and their promoter and regulatory elements. In some embodiments, the assays according to the following method are used in order to detect methylation within one or more genes selected from the group consisting of signature panels described herein wherein said methylated nucleic acids are present in a solution further comprising an excess of background DNA, wherein the background DNA is present in between about 100 to 1000 times, about 100 to 10000 times, about 100 to 100000 times, about 1000 to 10000 times, about 1000 to 100000 times, or about 10000 to 100000 times, the concentration of the DNA to be detected. In some embodiments, the concentration of DNA to be detected is greater than about 100000 times the background DNA concentration. In some embodiments, the method comprises contacting a nucleic acid sample obtained from a subject with at least one reagent or a series of reagents (e.g., that distinguishes between methylated and non-methylated CpG dinucleotides within the target nucleic acid).

A tumor or colon cell proliferative disorder, as described herein, may be selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

A signature panel comprising informative methylated regions may be selected according to the purpose of the intended assay. For targeted methods, primer pairs may be designed based on the set of intended target regions. In some embodiments, the set of regions comprises at least one, at least two, at least three, or more than three of the regions listed in Table 1. In some embodiments, the set of regions comprise all the regions listed in Table 1.

In some embodiments, the set of methyl regions associated with colorectal cancer is selected from Table 1.

In some embodiments, the cancer panel comprises regions selected from at least one, at least two, at least three, or more than three of ITGA4, EMBP1, TMEM163, SFMBT2, ELMO1, ZNF543, SFMBT2, CHST10, CCNA1, BEND4, KRBA1, S1PR1, PPP1R16B, IKZF1, LONRF2, ZFP82, and FLT3 (e.g., wherein the tumor is colorectal cancer). In some embodiments, the cancer panel comprises all the regions listed in Table 1. In some embodiments, the probes are directed to sequences selected from at least one, at least two, at least three, or more than three of ITGA4, EMBP1, TMEM163, SFMBT2, ELMO1, ZNF543, SFMBT2, CHST10, CCNA1, BEND4, KRBA1, S1PR1, PPP1R16B, IKZF1, LONRF2, ZFP82, and FLT3.

TABLE 1

Methyl Region (Gene ID; chromosome: region start-position end)

ITGA4; chr2: 181457004-181457950
EMBP1; chr1: 121519076-121519744
TMEM163; chr2: 134718243-134719428
SFMBT2; chr10: 7408046-7408953
ELMO1; chr7: 37448612-37449471
ZNF543; chr19: 57320164-57320845
SFMBT2; chr10: 7410025-7411008
CHST10; chr2: 100417269-100417795
ELMO1; chr7: 37447852-37448217
CCNA1; chr13: 36431498-36432414
BEND4; chr4: 42150707-42153216
KRBA1; chr7: 149714695-149715338
S1PR1; chr1: 101236505-101237190
PPP1R16B; chr20: 38805341-38807221
IKZF1; chr7: 50304053-50304944
LONRF2; chr2: 100322082-100322599
ZFP82; chr19: 36418330-36418931
FLT3; chr13: 28099881-28100943
FBN1; chr15: 48644595-48646444
FLI1; chr11: 128693042-128694372

In some embodiments, the method further comprises quantifying the methylation signals, wherein a number in excess of a pre-determined threshold is indicative of a colon cell proliferative disorder. In some embodiments, the quantifying and comparing are performed independently for each of the sites methylated in a colon cell proliferative disorder. Accordingly, a count of positive tumor signals may be established for each site. In some embodiments, the method further comprises determining a proportion of the sequencing reads containing tumor signals, wherein the proportion in excess of a threshold is indicative of a colon cell proliferative disorder. In some embodiments, the determining is performed independently for each of the sites methylated in a colon cell proliferative disorder.

The term "threshold", as used herein, generally refers to a value that is selected to discriminate, separate, or distinguish between two populations of subjects. In some embodiments, the threshold discriminates methylation status between a disease (e.g., malignant) state, and a non-disease (e.g., healthy) state. In some embodiments, the threshold discriminates between stages of disease (e.g., stage 1, stage 2, stage 3, or stage 4). Thresholds may be set according to the disease in question, and may be based on earlier analysis, e.g., of a training set or determined computationally on a set of inputs having known characteristic (e.g., healthy, disease, or stage of disease). Thresholds may also be set for a gene region according to the predictive value of methylation at a particular site. Thresholds may be different for each methylation site, and data from multiple sites may be combined in the end analysis.

In some embodiments, of the forgoing methods, the cancer panel comprises regions selected from at least one, at least two, at least three, or more than three of ITGA4, TMEM163, SFMBT2, ELMO1, ZNF543, CHST10, CCNA1, BEND4, KRBA1, S1PR1, and PPP1R16B (e.g., wherein the tumor is colorectal cancer). In some embodiments, the cancer panel comprises one or more of the regions listed in Table 2. In some embodiments, the probes are directed to sequences selected from at least one, at least two, at least three, or more than three of ITGA4, TMEM163, SFMBT2, ELMO1, ZNF543, CHST10, CCNA1, BEND4, KRBA1, S1PR1, and PPP1R16B.

TABLE 2

Methyl Region (Gene ID; chromosome: position start-position end)

ITGA4; chr2: 181457004-181457950
TMEM163; chr2: 134718243-134719428
SFMBT2; chr10: 7408046-7408953
ELMO1; chr7: 37448612-37449471
ZNF543; chr19: 57320164-57320845
SFMBT2; chr10: 7410025-7411008
CHST10; chr2: 100417269-100417795
ELMO1; chr7: 37447852-37448217
CCNA1; chr13: 36431498-36432414
BEND4; chr4: 42150707-42153216
KRBA1; chr7: 149714695-149715338
S1PR1; chr1: 101236505-101237190
PPP1R16B; chr20: 38805341-38807221

In some embodiments, the cancer panel comprises regions selected from at least one, at least two, at least three, or more than three of EMBP1, TMEM163, SFMBT2, ELMO1, ZNF543, CHST10, CCNA1, BEND4, KRBA1, S1PR1, and PPP1R16B (e.g., wherein the tumor is colorectal cancer). In some embodiments, the cancer panel comprises one or more of the regions listed in Table 3. In some embodiments, the probes are directed to sequences selected from at least one, at least two, at least three, or more than three of EMBP1, TMEM163, SFMBT2, ELMO1, ZNF543, CHST10, CCNA1, BEND4, KRBA1, S1PR1, and PPP1R16B.

TABLE 3

Methyl Region (Gene ID; chromosome: position start-position end)

EMBP1; chr1: 121519076-121519744
TMEM163; chr2: 134718243-134719428
SFMBT2; chr10: 7408046-7408953

TABLE 3-continued

Methyl Region (Gene ID; chromosome: position start-position end)

ELMO1; chr7: 37448612-37449471
ZNF543; chr19: 57320164-57320845
SFMBT2; chr10: 7410025-7411008
CHST10; chr2: 100417269-100417795
ELMO1; chr7: 37447852-37448217
CCNA1; chr13: 36431498-36432414
BEND4; chr4: 42150707-42153216
KRBA1; chr7: 149714695-149715338
S1PR1; chr1: 101236505-101237190
PPP1R16B; chr20: 38805341-38807221

In some embodiments, the cancer panel comprises regions selected from at least one, at least two, at least three, or more than three of ITGA4, EMBP1, TMEM163, SFMBT2, ELMO1, ZNF543, CHST10, CCNA1, BEND4, KRBA1, and S1PR1, and the tumor is colorectal cancer. In some embodiments, the cancer panel comprises one or more of the regions listed in Table 4. In some embodiments, the probes are directed to sequences selected from at least one, at least two, at least three, or more than three of ITGA4, EMBP1, TMEM163, SFMBT2, ELMO1, ZNF543, CHST10, CCNA1, BEND4, KRBA1, and S1PR1.

TABLE 4

Methyl Region (Gene ID; chromosome: position start-position end)

ITGA4; chr2: 181457004-181457950
EMBP1; chr1: 121519076-121519744
TMEM163; chr2: 134718243-134719428
SFMBT2; chr10: 7408046-7408953
ELMO1; chr7: 37448612-37449471
ZNF543; chr19: 57320164-57320845
SFMBT2; chr10: 7410025-7411008
CHST10; chr2: 100417269-100417795
ELMO1; chr7: 37447852-37448217
CCNA1; chr13: 36431498-36432414
BEND4; chr4: 42150707-42153216
KRBA1; chr7: 149714695-149715338
S1PR1; chr1: 101236505-101237190

In some embodiments, the cancer panel comprises regions selected from at least one, at least two, at least three, or more than three of ITGA4, EMBP1, TMEM163, SFMBT2, ELMO1, and ZNF543, and the tumor is colorectal cancer. In some embodiments, the cancer panel comprises the regions listed in Table 5. In some embodiments, the probes are directed to sequences selected from at least one, at least two, at least three, or more than three of ITGA4, EMBP1, TMEM163, SFMBT2, ELMO1, and ZNF5431.

TABLE 5

Methyl Region (Gene ID; chromosome: position start-position end)

ITGA4; chr2: 181457004-181457950
EMBP1; chr1: 121519076-121519744
TMEM163; chr2: 134718243-134719428
SFMBT2; chr10: 7408046-7408953
ELMO1; chr7: 37448612-37449471
ZNF543; chr19: 57320164-57320845

In some embodiments, the cancer panel comprises one or more of regions ITGA4 and EMBP1 (e.g., wherein the tumor is colorectal cancer). In some embodiments, the cancer panel comprises one or more of the regions listed in Table 6. In some embodiments, the probes are directed to sequences comprising ITGA4 and EMBP1.

TABLE 6

| Methyl Region (Gene ID; chromosome: position start-position end) |
| --- |
| ITGA4; chr2: 181457004-181457950 |
| EMBP1; chr1: 121519076-121519744 |

In some embodiments of the forgoing methods, the cancer panel comprises regions selected from at least one, at least two, at least three, or more than three of KZF1, KCNQ5, ELMO1, CHST2, PRKCB, FLI1, CLIP4, ELOVL5, FAM72B, ST3GAL1, ZEB2 NR3C1, ITGA4, GALNT14, CHST11, PPP1R16B, MGAT3, ZNF264, BEND4, IRF4, LOC100130992, CHST11, CHST15, RASSF2, EMILIN2, TMEM163, CHST10, and HCK (e.g., wherein the tumor is colorectal cancer). In some embodiments, the cancer panel comprises one or more of the regions listed in Table 7. In some embodiments, the probes are directed to sequences selected from at least one, at least two, at least three, or more than three of IKZF1, KCNQ5, ELMO1, CHST2, PRKCB, FLI1, CLIP4, ELOVL5, FAM72B, ST3GAL1, ZEB2 NR3C1, ITGA4, GALNT14, CHST11, PPP1R16B, MGAT3, ZNF264, BEND4, IRF4, LOC100130992, CHST11, CHST15, RASSF2, EMILIN2, TMEM163, CHST10, and HCK.

TABLE 7

| Methyl Region (Gene ID; chromosome: position start-position end) |
| --- |
| IKZF1; chr7: 50303445-50305526 |
| KCNQ5; chr6: 72620772-72623556 |
| ELMO1; chr7: 37447220-37450201 |
| CHST2; chr3: 143118680-143121423 |
| PRKCB; chr16: 23835445-23837405 |
| FLI1; chr11: 128691887-128696541 |
| CLIP4; chr2: 29114801-29116249 |
| ELOVL5; chr6: 53347501-53349589 |
| FAM72B; chr1: 121183841-121185542 |
| ST3GAL1; chr8: 133569551-133572891 |
| ZEB2; chr2: 144515419-144518700 |
| NR3C1; chr5: 143401827-143405879 |
| ITGA4; chr2: 181456334-181458768 |
| GALNT14; chr2: 31137019-31139128 |
| CHST11; chr12: 104456187-104457751 |
| PPP1R16B; chr20: 38804664-38807496 |
| MGAT3; chr22: 39457251-39458214 |
| ZNF264; chr19: 57191322-57192160 |
| BEND4; chr4: 42150430-42151135 |
| IRF4; chr6: 390976-392639 |
| LOC100130992; chr10: 22252249-22254125 |
| CHST11; chr12: 104457871-104459556 |
| CHST15; chr10: 124091538-124093818 |
| RASSF2; chr20: 4822195-4823943 |
| EMILIN2; chr18: 2846938-2848432 |
| TMEM163; chr2: 134717473-134719807 |
| CHST10; chr2: 100416426-100418154 |
| HCK; chr20: 32052182-32053208 |

In some embodiments of the forgoing methods, the cancer panel comprises regions selected from at least one, at least two, at least three, or more than three of IKZF1, KCNQ5, ELMO1, CHST2, PRKCB, FLI1, CLIP4, ELOVL5, FAM72B, ST3GAL1, ZEB2 NR3C1, ITGA4, GALNT14, CHST11, PPP1R16B, MGAT3, ZNF264, BEND4, and IRF4 (e.g., wherein the tumor is colorectal cancer). In some embodiments, the cancer panel comprises one or more of the regions listed in Table 8. In some embodiments, the probes are directed to sequences selected from at least one, at least two, at least three, or more than three of IKZF1, KCNQ5, ELMO1, CHST2, PRKCB, FLI1, CLIP4, ELOVL5, FAM72B, ST3GAL1, ZEB2 NR3C1, ITGA4, GALNT14, CHST11, PPP1R16B, MGAT3, ZNF264, BEND4, and IRF4.

TABLE 8

| Methyl Region (Gene ID; chromosome: position start-position end) |
| --- |
| IKZF1; chr7: 50303445-50305526 |
| KCNQ5; chr6: 72620772-72623556 |
| ELMO1; chr7: 37447220-37450201 |
| CHST2; chr3: 143118680-143121423 |
| PRKCB; chr16: 23835445-23837405 |
| FLI1; chr11: 128691887-128696541 |
| CLIP4; chr2: 29114801-29116249 |
| ELOVL5; chr6: 53347501-53349589 |
| FAM72B; chr1: 121183841-121185542 |
| ST3GAL1; chr8: 133569551-133572891 |
| ZEB2; chr2: 144515419-144518700 |
| NR3C1; chr5: 143401827-143405879 |
| ITGA4; chr2: 181456334-181458768 |
| GALNT14; chr2: 31137019-31139128 |
| CHST11; chr12: 104456187-104457751 |
| PPP1R16B; chr20: 38804664-38807496 |
| MGAT3; chr22: 39457251-39458214 |
| ZNF264; chr19: 57191322-57192160 |
| BEND4; chr4: 42150430-42151135 |
| IRF4; chr6: 390976-392639 |

In some embodiments of the forgoing methods, the cancer panel comprises regions selected from at least one, at least two, at least three, or more than three of IKZF1, KCNQ5, ELMO1, CHST2, PRKCB, FLI1, CLIP4, ELOVL5, FAM72B, and ST3GAL1 (e.g., wherein the tumor is colorectal cancer). In some embodiments, the cancer panel comprises one or more of the regions listed in Table 9. In some embodiments, the probes are directed to sequences selected from at least one, at least two, at least three, or more than three of IKZF1, KCNQ5, ELMO1, CHST2, PRKCB, FLI1, CLIP4, ELOVL5, FAM72B, and ST3GAL1.

TABLE 9

| Methyl Region (Gene ID; chromosome: position start-position end) |
| --- |
| IKZF1; chr7: 50303445-50305526 |
| KCNQ5; chr6: 72620772-72623556 |
| ELMO1; chr7: 37447220-37450201 |
| CHST2; chr3: 143118680-143121423 |
| PRKCB; chr16: 23835445-23837405 |
| FLI1; chr11: 128691887-128696541 |
| CLIP4; chr2: 29114801-29116249 |
| ELOVL5; chr6: 53347501-53349589 |
| FAM72B; chr1: 121183841-121185542 |
| ST3GAL1; chr8: 133569551-133572891 |

In some embodiments of the forgoing methods, the cancer panel comprises regions selected from at least one, at least two, at least three, or more than three of IKZF1, KCNQ5, ELMO1, CHST2, PRKCB, and FLI1 (e.g., wherein the tumor is colorectal cancer). In some embodiments, the cancer panel comprises one or more of the regions listed in Table 10. In some embodiments, the probes are directed to sequences selected from at least one, at least two, at least three, or more than three of IKZF1, KCNQ5, ELMO1, CHST2, PRKCB, and FLI1.

TABLE 10

| Methyl Region (Gene ID; chromosome: position start-position end) |
| --- |
| IKZF1; chr7: 50303445-50305526 |
| KCNQ5; chr6: 72620772-72623556 |
| ELMO1; chr7: 37447220-37450201 |
| CHST2; chr3: 143118680-143121423 |
| PRKCB; chr16: 23835445-23837405 |
| FLI1; chr11: 128691887-128696541 |

In some embodiments of the forgoing methods, the cancer panel comprises regions selected from at least one, at least two, or at least three of IKZF1, KCNQ5, and ELMO1 (e.g., wherein the tumor is colorectal cancer). In some embodiments, the cancer panel comprises one or more of the regions listed in Table 11. In some embodiments, the probes are directed to sequences selected from at least one, at least two, or at least three of IKZF1, KCNQ5, and ELMO1.

TABLE 11

Methyl Region (Gene ID; chromosome: position start-position end)

IKZF1; chr7: 50303445-50305526
KCNQ5; chr6: 72620772-72623556
ELMO1; chr7: 37447220-37450201

In an aspect, the present disclosure provides a method for identifying a methylation signature indicative of a biological characteristic, the method comprising: obtaining data for a population comprising a plurality of genomic methylation data sets associated with colon cell proliferative disorder status, each of said genomic methylation data sets associated with biological information for a corresponding sample, segregating the methylation data sets into a first group corresponding to one tissue or cell type possessing the biological characteristic and a second group corresponding to a plurality of tissue or cell types not possessing the biological characteristic, matching methylation data from the first group to methylation data from the second group on a site-by-site basis across the genome, identifying a set of CpG sites on a site-by-site basis across the genome that meet a pre-determined threshold for establishing differential methylation between the first and second groups, identifying, using the set of CpG sites, target genomic regions comprising at least one, at least two, at least three, or more than three differentially methylated CpGs within about 30 to 300 bp that meet said pre-determined criteria, to identify differentially methylated genomic regions that provide the methylation signature indicative of the biological characteristic associated with the presence of a colon cell proliferative disorder.

In some examples, the target genomic region comprises at least one, at least two, at least three, or more than three differentially methylated CpG sites within a region having a length of about 30 to 150 bp, about 40 to 150 bp, about 50 to 150 bp, about 75 to 150 bp, about 100 to 150 bp, about 150 to 300 bp, about 150 to 250 bp, about 150 to 200 bp, about 200 to 300 bp, or about 250 to 300 bp.

In some examples, the target genomic region comprises at least four differentially methylated CpG sites, at least four differentially methylated CpG sites, at least five differentially methylated CpG sites, at least six differentially methylated CpG sites, at least seven differentially methylated CpG sites, at least eight differentially methylated CpG sites, at least nine differentially methylated CpG sites, at least ten differentially methylated CpG sites, at least 12 differentially methylated CpG sites, or at least 15 differentially methylated CpG sites.

In some embodiments, the method further comprises validating the extended target genomic regions by testing for differential methylation within the extended target genomic regions using DNA from at least one independent sample possessing the biological trait and DNA from at least one independent sample not possessing the biological sample.

In some embodiments, the identifying further comprises limiting the set of CpG sites to CpG sites that further exhibit differential methylation with peripheral blood mononuclear cells from a reference or control sample.

In some embodiments, the pre-determined threshold is at least about 50% methylation in the first group.

In some embodiments, the pre-determined threshold is a difference in average methylation between the first and second groups of at least about 0.3.

In some embodiments, the biological trait comprises malignancy.

In some embodiments, the biological trait comprises a cancer type.

In some embodiments, the biological trait comprises a cancer stage.

In some embodiments, the biological trait comprises a cancer classification.

In some embodiments, the cancer classification comprises a cancer grade.

In some embodiments, the cancer classification comprises a histological classification.

In some embodiments, the biological trait comprises a metabolic profile.

In some embodiments, the biological trait comprises a mutation.

In some embodiments, the mutation is a disease-associated mutation.

In some embodiments, the biological trait comprises a clinical outcome.

In some embodiments, the biological trait comprises a drug response.

In some embodiments, the method further comprises designing a plurality of PCR primer pairs to amplify portions of the extended target genomic regions, each of the portions comprising at least one differentially methylated CpG site.

In some embodiments, the designing of the plurality of primer pairs comprises converting non-methylated cytosines into uracil, to simulate cytosine-to-uracil conversion, and designing the primer pairs using the converted sequence.

In some embodiments, the primer pairs are designed to have a methylation bias.

In some embodiments, the primer pairs are methylation-specific.

In some embodiments, the primer pairs have no CpG residues within them having no preference for methylation status.

In an aspect, the present disclosure provides a method for synthesizing primer pairs specific to a methylation signature, the method comprising: performing a method of the present disclosure, and synthesizing the designed primer pairs.

IV. Nucleic Acid Conversion and Methylation Sequencing

A. Nucleic Acid Treatment

Various methods are available for methylation sequencing that include chemical-based and enzymatic-based conversion of nucleic acid bases to distinguish methylated from unmethylated cytosines in a nucleic acid sequence. These assays allow for determination of the methylation state of one or a plurality of CpG dinucleotides (e.g., CpG islands) within a DNA sequence. Such assays may comprise, among other techniques, DNA sequencing of bisulfite-treated DNA, or enzymatic-treated DNA, polymerase chain reaction (PCR) (for sequence-specific amplification), quantitative PCR (qPCR), or digital droplet PCR (ddPCR), Southern blot analysis. In various examples, DNA in a biological sample is treated in such a manner that cytosine bases which are unmethylated at 5'-position are converted to uracil, thymine, or another base which is dissimilar to cytosine in terms of hybridization behavior. This may be referred to as "conversion".

In some embodiments, the reagent converts cytosine bases which are unmethylated at 5'-position to uracil, thymine, or another base which is dissimilar to cytosine in terms of hybridization behavior.

Bisulfite modification of DNA generally refers to a tool used to assess CpG methylation status. A frequently used method for analyzing DNA for the presence of 5-methylcytosine (5-mC) is based upon the reaction of bisulfite with cytosine whereby, upon subsequent alkaline desulfonation, cytosine is converted to uracil which corresponds to thymine in its base pairing behavior. For example, genomic sequencing has been adapted for analysis of DNA methylation patterns and 5-methylcytosine distribution by using bisulfite treatment (e.g., as described by Frommer et al., Proc. Natl. Acad. Sci. USA 89:1827-1831, 1992, the contents of which are incorporated herein by reference). Significantly, however, 5-methylcytosine remains unmodified under these conditions. Consequently, the original DNA is converted in such a manner that methylcytosine (methyl-C), which originally could not be distinguished from cytosine by its hybridization behavior, can now be detected as the only remaining cytosine using various molecular biological techniques, for example, by amplification and hybridization, or by sequencing. In various examples, other reagents may affect the same result as bisulfite modification useful for methylation sequencing.

One frequently used direct sequencing method employs bisulfite-treated DNA amplified with PCR useful with whole-genome bisulfite sequencing (WGBS) or targeted bisulfite sequencing.

Targeted Bisulfite Sequencing may refer to a commercially available NGS method used to evaluate site-specific DNA methylation changes. Probes are designed to be strand-specific as well as bisulfite-specific. Both methylated and unmethylated sequences are amplified. The process is similar to pyrosequencing but offers a much higher throughput overall. In some embodiments, next-generation sequencing platforms are used to deliver large amounts of useful DNA methylation information (e.g., EPIGENTEK, Farmingdale, NY and ZYMO RESEARCH, Irvine, CA). The methylation analysis at single-base resolution of individual cytosine in DNA may be facilitated by bisulfite treatment of DNA followed by PCR amplification of targeted region, library construction, and sequencing of the amplicon regions. Specific primers may be designed for the region of interest and cytosine methylation changes are evaluated within that region. Each DNA methylation site of interest may be assessed at high-sequencing depth of coverage for accurate, quantitative and single-base resolution data output.

Enzymatic methyl sequencing (EM-seq) may rely on enzymatic conversion of nucleic acids for methylome analysis. Data may suggest that the process of generating EM-seq libraries does not damage DNA in the same way as bisulfite sequencing. EM-seq libraries may give higher PCR yields despite using fewer PCR cycles for all DNA input amounts, indicating that less DNA is lost during enzymatic treatment and library preparation, as compared to whole genome bisulfite sequencing (WGBS). Reduced PCR cycles, in turn, may translate into more complex libraries and fewer PCR duplicates during sequencing. EM-seq libraries also may have larger average insert sizes than WGBS which further supports the fact that DNA remains intact. In the EM-seq workflow, TET2 oxidizes 5-mC and 5-hmC, providing protection from deamination by APOBEC in the next operation. In contrast, unmodified cytosines are deaminated to uracils. In some embodiments, the targeted method comprises enzymatic conversion of nucleic acid (TEM-seq). In some embodiments, the methylation sequencing methods are accomplished with the NEBNEXT® Enzymatic Methyl-seq (New England Biolabs, Ipswich, MA) which is useful for identification of 5mC and 5hmC.

In another example, 5hmC may be also detected using TET-assisted bisulfite sequencing (TAB-seq) (e.g., as described by Yu, M., et al. (2012). Nat. Protoc. 7, 2159-2170, the contents of which are incorporated herein by reference) (WiseGene; Illumina®). Fragmented DNA may be enzymatically modified using sequential T4 Phage ß-glucosyltransferase (T4-BGT), and then Ten-eleven translocation (TET) dioxygenase treatments before the addition of sodium bisulfite. T4-BGT glucosylates 5hmC to form beta-glucosyl-5-hydroxymethylcytosine (5ghmC) and TET is then used to oxidize 5mC to 5caC. Only 5ghmC is protected from subsequent deamination by sodium bisulfite and this enables 5hmC to be distinguished from 5mC by sequencing.

Oxidative bisulfite sequencing (oxBS) provides another method to distinguish between 5mC and 5hmC (e.g., as described by Booth, M. J., et al., 2012 Science 336:934-937, the contents of which are incorporated herein by reference). The oxidation reagent potassium perruthenate converts 5hmC to 5-formylcytosine (5fC) and subsequent sodium bisulfite treatment deaminates 5fC to uracil. 5mC remains unchanged and can therefore be identified using this method.

APOBEC-coupled epigenetic sequencing (ACE-seq) excludes bisulfite conversion altogether and relies on enzymatic conversion to detect 5hmC (e.g., as described by Schutsky, E. K., et al., Nat. Biotechnol., 2018 Oct. 8, the contents of which are incorporated herein by reference). With this method, T4-BGT glucosylates 5hmC to 5ghmC and protects it from deamination by Apolipoprotein B mRNA editing enzyme subunit 3A (APOBEC3A). Cytosine and 5mC are deaminated by APOBEC3A and sequenced as thymine.

In another example, a bisulfite-free and base-level-resolution sequencing method, TET-assisted pyridine borane sequencing (TAPS), may be used for detection of 5mC and 5hmC. TAPS combines ten-eleven translocation (TET) oxidation of 5mC and 5hmC to 5-carboxylcytosine (5caC) with pyridine borane reduction of 5caC to dihydrouracil (DHU). Subsequent PCR converts DHU to thymine, enabling a C-to-T transition of 5mC and 5hmC. TAPS detects modifications directly with high sensitivity and specificity, without affecting unmodified cytosines. (e.g., as described by Liu, Y., et al. Nat Biotechnol. 2019 April; 37 (4): 424-429, the contents of which are incorporated herein by reference).

TET-assisted 5-methylcytosine sequencing (TAmC-seq) enriches for 5mC loci and utilizes two sequential enzymatic reactions followed by an affinity pull-down (e.g., as described by Zhang, L. 2013, Nat Commun 4:1517, the contents of which are incorporated herein by reference). Fragmented DNA is treated with T4-BGT which protects 5hmC by glucosylation. The enzyme mTET1 is then used to oxidize 5mC to 5hmC, and T4-BGT labels the newly formed 5hmC using a modified glucose moiety (6-N3-glucose). Click chemistry is used to introduce a biotin tag which enables enrichment of 5mC-containing DNA fragments for detection and genome wide profiling.

B. Next-Generation Sequencing

In some embodiments, the generating of sequencing reads is performed by next-generation sequencing. This may permit a high depth of reads to be achieved for a given region.

These may be high-throughput methods that include, for example, Illumina® (Solexa) sequencing, DNB-Sequencer T7 (DNBSEQ®) or G400 (MGI Tech Co., Ltd), GenapSys® sequencing (GenapSys, Inc.), Roche 454 sequencing (Roche Sequencing Solutions, Inc.), Ion Torrent sequencing (Thermo Fisher Scientific), and SOLID sequencing (Thermo Fisher Scientific®). The number of sequencing reads may be adjusted depending on DNA input amount and depth of data required for analysis.

In some embodiments, the generating of sequencing reads is performed simultaneously for samples obtained from multiple patients, wherein the cell-free nucleic acid fragments are barcoded for each patient. This permits parallel analysis of a plurality of patients in one sequencing run.

In another aspect, the present disclosure provides a kit for detecting a tumor comprising reagents for carrying out the aforementioned method, and instructions for detecting the tumor signals. Reagents may include, for example, primer sets, PCR reaction components, and/or sequencing reagents.

C. Targeted Sequencing

In targeted methylation sequencing approaches, targeted regions in a biological sample such as cfDNA are analyzed in order to determine the methylation state of the target gene sequences. In some embodiments, the target region comprises, or hybridizes under stringent conditions to, contiguous nucleotides of target regions of interest, such as at least about 16 contiguous nucleotides of a target region of interest. In different examples, targeted sequencing may be accomplished using hybridization capture and amplicon sequencing approaches.

D. Hybridization Capture

The hybridization method provided herein may be used in various formats of nucleic acid hybridizations, such as in-solution hybridization and such as hybridization on a solid support (e.g., Northern, Southern and in situ hybridization on membranes, microarrays and cell/tissue slides). In particular, the method is suitable for in-solution hybrid capture for target enrichment of certain types of genomic DNA sequences (e.g., exons) employed in targeted next-generation sequencing. For hybrid capture approaches, a cell-free nucleic acid sample is subjected to library preparation. As used herein, "library preparation" comprises end-repair, A-tailing, adapter ligation, or any other preparation performed on the cell-free DNA to permit subsequent sequencing of DNA. In certain examples, a prepared cell-free nucleic acid library sequence contains adapters, sequence tags, index barcodes that are ligated onto cell-free nucleic acid sample molecules. Various commercially available kits are available to facilitate library preparation for next-generation sequencing approaches. Next-generation sequencing library construction may comprise preparing nucleic acids targets using a coordinated series of enzymatic reactions to produce a random collection of DNA fragments, of specific size, for high throughput sequencing. Advances and the development of various library preparation technologies have expanded the application of next-generation sequencing to fields such as transcriptomics and epigenetics.

Improvements in sequencing technologies have resulted in changes and improvements to library preparation. Next-generation sequencing library preparation kits, developed by companies such as Agilent®, Bioo Scientific®, Kapa Biosystems®, New England Biolabs®, Illumina®, Life Technologies®, Pacific Biosciences®, and Roche® provide consistency and reproducibility to various molecular biology reactions that ensure compatibility with the latest NGS instrument technology.

In various examples for targeted capture gene panels, various library preparation kits may be selected from the group consisting of Nextera Flex (Illumina®), Illumina® DNA Prep (Illumina®), Ion AmpliSeq® (Thermo Fisher Scientific®), GeneXus® (Thermo Fisher Scientific®), Agilent ClearSeq (Illumina®), Agilent® SureSelect® Capture (Illumina®), Archer® FusionPlex® (Illumina®), Bioo Scientific® NEXTflex® (Illumina®), IDT® xGen (Illumina®), Illumina® TruSight® (Illumina®), NimbleGen® SeqCap® (Illumina®), and Qiagen® GeneRead® (Illumina®).

In some embodiments, the hybrid capture method is performed on the prepared library sequences using specific probes. In some embodiments, the term "specific probe", as used herein, generally refers to a probe that is specific for known methylation sites. In some embodiments, the specific probes are designed based on using human genome as a reference sequence and using specified genomic regions known to have methylation sites as target sequences. Specifically, the genomic region known to have methylation sites may comprise at least one of the following: a promoter region, a CpG island region, a CGI shore region, and a imprinted gene region. Therefore, when carrying out the hybrid capture by using the specific probes of some embodiments, the sequences in the sample genome which are complimentary to the target sequences, e.g., regions in the sample genome known to have methylation sites (which are also referred to as "specified genomic regions" herein) may be captured efficiently.

According to an example, the methylated regions described herein are used for designing the specific probes. In some embodiments, the specific probes are designed using commercially available methods such as for example an eArray system. The length of the probes may be sufficient to hybridize with sufficient specificity to the methylated region of interest. In various examples, the probe is a 10-mer, 11-mer, 12-mer, 13-mer, 14-mer 15-mer, 16-mer, 17-mer, 18-mer, 19-mer, or 20-mer.

The regions listed in above Tables 1-11 are screened out by making use of database resources (such as gene ontology). According to the principle of complementary base pairing, a single-stranded capture probe may be combined with a single-stranded target sequence complementarily, so as to capture the target region successfully. In some embodiments, the designed probes may be designed as a solid capture chip (wherein the probes are immobilized on a solid support) or be designed as a liquid capture chip (wherein the probes are free in the liquid), however, limited by various factors, such as probe length, probe density, and high cost, etc., the solid capture chip is rarely used, while the liquid capture chip is used more frequently.

In some embodiments, compared with normal sequences (where the average content of A, T, C, and G base is 25% each, respectively), GC-rich sequences (where the content of GC bases is higher than 60%) in nucleic acid may lead to the reduction of capture efficiency because of the molecular structure of C and G base. For the key research regions, for example, CGI regions (CpG Island), it may be recommended to design an increased amount of the probes to obtain sufficient and accurate CGI data.

E. Amplicon-Based Sequencing

Fragments of the converted DNA may be amplified. In some embodiments, the amplifying is performed with primers designed to anneal to methylation converted target sequences having at least one methylated site therein. Methylation sequencing conversion results in unmethylated cytosines being converted to uracil, while 5-methylcytosine is unaffected. "Converted target sequences" are thus understood to be sequences in which cytosines known to be methylation sites are fixed as "C" (cytosine), while cytosines known to be unmethylated are fixed as "U" (uracil; which may be treated as "T" (thymine) for primer design purposes).

In various examples, the source of the DNA is cell-free DNA from whole blood, plasma, serum, or genomic DNA extracted from cells or tissue. In some embodiments, the size of the amplified fragment is between about 100 and 200 base pairs in length. In some embodiments, the DNA source is extracted from cellular sources (e.g., tissues, biopsies, cell lines), and the amplified fragment is between about 100 and 350 base pairs in length. In some embodiments, the amplified fragment comprises at least one 20 base pair sequence comprising at least one, at least two, at least three, or more than three CpG dinucleotides. The amplification may be performed using sets of primer oligonucleotides according to the present disclosure, and may use a heat-stable polymerase. The amplification of several DNA segments may be performed simultaneously in one and the same reaction vessel. In some embodiments, two or more fragments are amplified simultaneously. For example, the amplification may be performed using a polymerase chain reaction (PCR).

Primers designed to target such sequences may exhibit a degree of bias towards converted methylated sequences. In some embodiments, the PCR primers are designed to be methylation specific for targeted methylation-sequencing applications. This may allow for greater sensitivity in some applications. For instance, primers may be designed to include a discriminatory nucleotide (specific to a methylated sequence following bisulfite conversion) positioned to achieve optimal discrimination, e.g., in PCR applications. The discriminatory may be positioned at the 3' ultimate or penultimate position.

In some embodiments, the primers are designed to amplify DNA fragments 75 to 350 bp in length. This is the general size range known for circulating DNA and optimizing primer design to take into account target size may increase the sensitivity of the method according to this example. The primers may be designed to amplify regions that are about 50 to 200, about 75 to 150, or about 100 or 125 bp in length.

In some embodiments of methods described herein, the methylation status of preselected CpG positions within the nucleic acid sequences may be detected by the amplicon-based approach using of methylation-specific primer oligonucleotides. The use of methylation status specific primers for the amplification of bisulfite treated DNA allows the differentiation between methylated and unmethylated nucleic acids. MSP primers pairs contain at least one primer which hybridizes to a converted CpG dinucleotide. Therefore, the sequence of said primers comprises at least one CpG, TpG, or CpA dinucleotide. MSP primers specific for non-methylated DNA contain a "T" at 3' position of the C in the CpG. Therefore, the base sequence of said primers may be required to comprise a sequence having a length of at least 18 nucleotides which hybridizes to a pretreated nucleic acid sequence and sequences complementary thereto, wherein the base sequence of said oligomers comprises at least one CpG, TpG, or CpA dinucleotide. In some embodiments, the MSP primers comprise between 2 and 5 CpG, TpG, or CpA dinucleotides. In some embodiments, the dinucleotides are located within 3' half of the primer, e.g., for a primer that is 18 bases in length, the specified dinucleotides are located within the first 9 bases from 3' end of the molecule. In addition to the CpG, TpG, or CpA dinucleotides, the primers may further comprise several methyl converted bases (e.g., cytosine converted to thymine, or on the hybridizing strand, guanine converted to adenosine). In some embodiments, the primers are designed so as to comprise no more than 2 cytosine or guanine bases.

In some embodiments, each of the regions is amplified in sections using multiple primer pairs. In some embodiments, these sections are non-overlapping. The sections may be immediately adjacent or spaced apart (e.g., spaced apart up to 10, 20, 30, 40, or 50 bp). Since target regions (including CpG islands, CpG shores, and/or CpG shelves) are usually longer than 75 to 150 bp, this example permits the methylation status of sites across more (or all) of a given target region to be assessed.

Primers may be designed for target regions using suitable tools such as Primer3, Primer3Plus, Primer-BLAST, etc. As discussed, bisulfite conversion results in cytosine converting to uracil and 5'-methyl-cytosine converting to thymine. Thus, primer positioning or targeting may make use of bisulfite converted methylate sequences, depending on the degree of methylation specificity required.

Target regions for amplification are designed to have at least 10 CpG dinucleotide methylation sites. In some examples, however, it may be advantageous to amplify regions having more than 10 CpG methylation site. For instance, a sequence read 300 bp long may have about 10, 20, 30, 40, or 50 CpG methylation sites that are methylated in a nucleic acid sample associated with a colon cell proliferative disorder. In various examples, the methylation regions identified in Tables 1-11 may have at least 25, 50, 100, 200, 300, 400, or 500 CpG methylation sites that are methylated in a nucleic acid sample associated with a colon cell proliferative disorder. In some embodiments, the primers are designed to amplify DNA fragments comprising 3 to 20 CpG methylation sites in a targeted region. Overall, this approach permits a larger number of methylation sites to be queried within a single sequencing read and provides additional certainty (exclusion of false positives) because multiple concordant methylations may be detected within a single sequencing read. In some embodiments, the tumor signals comprise more than two methylated regions selected from Tables 1-11. Detection of multiple tumor signals, in this example, can increase confidence in tumor detection. Such signals may be at the same or at different sites. In some embodiments, the detection of more than one of the tumor signals at the same region is indicative of a tumor.

In some embodiments, the number of CpG sites in an identified methylated region may be modeled between two populations having a different characteristic of a colon cell proliferative disorder to identify a methylation threshold where the number of CpG sites in a region that exceeds the threshold is indicative of a colon cell proliferative disorder.

In various examples, the number of CpG sites in an identified methylated region that indicates colorectal cancer is at least 2, 3, 4, 5, 6, 7, 8, 9, 10, 11, 12, 13, 14, 15, 16, 17, or 18, where the presence of methylated CpGs that exceeds this identified number is indicative of colorectal cancer and may be used as an input feature into a machine learning model used as a classifier to stratify a population into healthy individuals and those having colorectal cancer.

Detection of multiple tumor signals indicative of methylation at the same site in the genome, in this example, can increase confidence in tumor detection. Detection of methylation at adjacent sites in the genome, even if the signals are derived from different sequencing reads, can also increase confidence in tumor detection. This reflects another type of signal concordance. In some embodiments, the detection of adjacent or overlapping tumor signals across at least two different sequencing reads is indicative of a tumor. In some embodiments, the adjacent or overlapping tumor signals are within the same CpG island. In some embodiments, the detection of 3 to 34 proximal methylated sites in a cell-free DNA fragment is indicative of a tumor. In some embodiments, the detection of 3 to 34 methylated CpG sites in a fragment is used to identify a threshold to distinguish between a population of individuals having a characteristic (e.g., healthy, disease, or stage of disease). In some embodiments, the detection of about 4 to 10, about 4 to 15, about 10 to 20, about 15 to 20, about 15 to 25, about 20 to 25, about 20 to 34, about 25 to 34, or about 30 to 34 methylated proximal CpG sites in a read fragment is used to identify a threshold to distinguish between a population of individuals having a characteristic (e.g., healthy, disease, or stage of disease). As used herein, the term "proximal CpG site" refers to CpG sites that are adjacent or within about 2 to 10 CpG sites of each other and where the CpG sites on the same nucleic acid fragment in a cell-free nucleic acid sample.

In some embodiments, the amplification is performed with more than 100 primer pairs. The amplification may be performed with about 10, about 20, about 30, about 40, about 50, about 60, about 70, about 80, about 90, about 100, about 110, about 120, about 130, about 140, about 150, or more primer pairs. In some embodiments, the amplification is a multiplex amplification. Multiplex amplification permits large amount of methylation information to be gathered from many target regions in the genome in parallel, even from cfDNA samples in which DNA is generally not plentiful. The multiplexing may be scaled up to a platform such as Ion AmpliSeq®, in which, e.g., up to about 24,000 amplicons may be queried simultaneously. In some embodiments, the amplification is nested amplification. A nested amplification may improve sensitivity and specificity.

Further, another rapid and robust protocol for the parallel examination of multiple methylated sequences termed simultaneous targeted methylation sequencing (sTM-Seq). Key features of this technique include the elimination of the need for large amounts of high-molecular weight DNA and the nucleotide specific distinction of both 5-methylcytosine (5mC) and 5-hydroxymethylcytosine (5hmC). Moreover, sTM-Seq is scalable and may be used to investigate multiple loci in dozens of samples within a single sequencing run. Freely available web-based software and universal primers for multipurpose barcoding, library preparation, and customized sequencing make sTM-Seq affordable, efficient, and widely applicable (e.g., as described by Asmus, N. et al., Curr Protoc Hum Genet. 2019 April; 101(1), the contents of which are incorporated herein by reference).

Generally, the methods and systems provided herein are useful for preparation of cell-free polynucleotide sequences to a downstream application sequencing reaction. In some embodiments, a sequencing method is classic Sanger sequencing. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina®), Digital Gene Expression (Helicos®), next-generation sequencing, Single Molecule Sequencing by Synthesis (SMSS) (Helicos®), massively-parallel sequencing, Clonal Single Molecule Array (Solexa), shotgun sequencing, Maxim-Gilbert sequencing, primer walking, and any other sequencing methods.

Pyrosequencing may refer to a real-time sequencing technology based on luminometric detection of pyrophosphate release upon nucleotide incorporation which is suited for simultaneous analysis and quantification of the methylation degree of several CpG positions. After conversion of genomic DNA, a region of interest is amplified by polymerase chain reaction (PCR) with one of the two primers being biotinylated. The PCR-generated template is rendered single stranded and a Pyrosequencing primer is annealed to analyze quantitatively CpG positions. After bisulfite treatment and PCR, the degree of each methylation at each CpG position in a sequence is determined from the ratio of T and C signals reflecting the proportion of unmethylated and methylated cytosines at each CpG site in the original sequence.

V. Classifiers, Machine Learning Models, & Systems

In various examples, methylation sequencing features are used as input datasets into trained algorithms (e.g., machine learning models or classifiers) to find correlations between sequence composition and patient groups. Examples of such patient groups include presence of diseases or conditions, stages, subtypes, responders vs. non-responders, and progressors vs. non-progressors. In various examples, feature matrices are generated to compare samples obtained from individuals with known conditions or characteristics. In some embodiments, samples are obtained from healthy individuals, or individuals who do not have any of the known indications and samples from patients known to have cancer.

As used herein, relating to machine learning and pattern recognition, the term "feature" generally refers to an individual measurable property or characteristic of a phenomenon being observed. The concept of "feature" is related to that of explanatory variable used in statistical techniques such as for example, but not limited to, linear regression and logistic regression. Features are usually numeric, but structural features such as strings and graphs are used in syntactic pattern recognition.

The term "input features" (or "features"), as used herein, generally refers to variables that are used by the trained algorithm (e.g., model or classifier) to predict an output classification (label) of a sample, e.g., a condition, sequence content (e.g., mutations), suggested data collection operations, or suggested treatments. Values of the variables may be determined for a sample and used to determine a classification.

In various examples, input features of genetic data include: aligned variables that relate to alignment of sequence data (e.g., sequence reads) to a genome and non-aligned variables, e.g., that relate to the sequence content of a sequence read, a measurement of protein or autoantibody, or the mean methylation level at a genomic region. Input features may be genetic features such as, V-plot measures, FREE-C deconvolution, chromatin accessibility, and cfDNA measurement over a transcription start site. Metrics that may be used in methylation analysis include, but are not limited to, base wise methylation percent for CpG, CHG, CHH, conversion efficiency (100-mean methylation percent for CHH), hypomethylated blocks, methylation levels (global mean methylation for CPG, CHH, CHG, fragment length, fragment midpoint, and methylation levels in one or more genomic regions such as chrM, LINE1, or ALU), number of methylated CpGs per fragment, fraction of CpG methylation to total CpG per fragment, fraction of CpG methylation to total CpG per region, fraction of CpG methylation to total CpG in panel, dinucleotide coverage (normalized coverage of dinucleotide), evenness of coverage (unique CpG sites at 1× and 10× mean genomic coverage (for S4 runs), mean CpG coverage (depth) globally, and mean coverage at CpG islands, CGI shelves, CGI shores. These metrics may be used as feature inputs for machine learning methods and models.

For a plurality of assays, the system identifies feature sets to input into a trained algorithm (e.g., machine learning model or classifier). The system performs an assay on each molecule class and forms a feature vector from the measured values. The system inputs the feature vector into the machine learning model and obtains an output classification of whether the biological sample has a specified property.

In some embodiments, the machine learning model outputs a classifier capable of distinguishing between two or more groups or classes of individuals or features in a population of individuals or features of the population. In some embodiments, the classifier is a trained machine learning classifier.

In some embodiments, the informative loci or features of biomarkers in a cancer tissue are assayed to form a profile. Receiver-operating characteristic (ROC) curves may be generated by plotting the performance of a particular feature (e.g., any of the biomarkers described herein and/or any item of additional biomedical information) in distinguishing between two populations (e.g., individuals responding and not responding to a therapeutic agent). In some embodiments, the feature data across the entire population (e.g., the cases and controls) are sorted in ascending order based on the value of a single feature.

In various examples, the specified property is selected from healthy vs. cancer, disease subtype, disease stage, progressor vs. non-progressor, and responder vs. non-responder.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

A. Data Analysis

In some examples, the present disclosure provides a system, method, or kit having data analysis realized in software application, computing hardware, or both. In various examples, the analysis application or system comprises at least a data receiving module, a data pre-processing module, a data analysis module (which can operate on one or more types of genomic data), a data interpretation module, or a data visualization module. In some embodiments, the data receiving module can comprise computer systems that connect laboratory hardware or instrumentation with computer systems that process laboratory data. In some embodiments, the data pre-processing module can comprise hardware systems or computer software that performs operations on the data in preparation for analysis. Examples of operations that may be applied to the data in the pre-processing module include affine transformations, denoising operations, data cleaning, reformatting, or subsampling. A data analysis module, which may be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results.

In various examples, machine learning methods are applied to distinguish samples in a population of samples. In some embodiments, machine learning methods are applied to distinguish samples between healthy and advanced disease (e.g., adenoma) samples.

In some embodiments, the one or more machine learning operations used to train the prediction engine include one or more of: a generalized linear model, a generalized additive model, a non-parametric regression operation, a random forest classifier, a spatial regression operation, a Bayesian regression model, a time series analysis, a Bayesian network, a Gaussian network, a decision tree learning operation, an artificial neural network, a recurrent neural network, a convolutional neural network, a reinforcement learning operation, linear or non-linear regression operations, a support vector machine, a clustering operation, and a genetic algorithm operation.

In various examples, computer processing methods are selected from the group consisting of logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, and artificial neural networks.

In some examples, the methods disclosed herein can include computational analysis on nucleic acid sequencing data of samples from an individual or from a plurality of individuals.

B. Classifier Generation

In an aspect, the disclosed systems and methods provide a classifier generated based on feature information derived from methylation sequence analysis from biological samples of cfDNA. The classifier forms part of a predictive engine for distinguishing groups in a population based on sequence features identified in biological samples such as cfDNA.

In some embodiments, a classifier is created by normalizing the sequence information by formatting similar portions of the sequence information into a unified format and a unified scale; storing the normalized sequence information in a columnar database; training a prediction engine by applying one or more one machine learning operations to the stored normalized sequence information, the prediction engine mapping, for a particular population, a combination of one or more features; applying the prediction engine to the accessed field information to identify an individual associated with a group; and classifying the individual into a group.

In some embodiments, a hierarchy is created by normalizing the sequence information by formatting similar portions of the sequence information into a unified format and a unified scale; storing the normalized sequence information in a columnar database; training a prediction engine by applying one or more one machine learning operations to the stored normalized sequence information, the prediction engine mapping, for a particular population, a combination of one or more features; applying the prediction engine to the accessed field information to identify an individual associated with a group; and classifying the individual into a group.

Specificity, as used herein, generally refers to "the probability of a negative test result among those who are free from the disease". It may be calculated by the number of disease-free persons who tested negative divided by the total number of disease-free individuals.

In various examples, the model, classifier, or predictive test has a specificity of at least 40%, at least 45%, at least 50%, at least 55%, at least 60%, at least 65%, at least 70%, at least 75%, at least 80%, at least 85%, at least 90%, at least 95%, or at least 99%.

Sensitivity, as used herein, generally refers to "the probability of a positive test result among those who have the disease". It may be calculated by the number of diseased individuals who tested positive divided by the total number of diseased individuals.

In various examples, the model, classifier, or predictive test has a sensitivity of at least 40%, at least 45%, at least 50%, at least 55%, at least 60%, at least 65%, at least 70%, at least 75%, at least 80%, at least 85%, at least 90%, at least 95%, or at least 99%.

Positive predictive value, as used herein, generally refers to "the probability of a positive test result being correct". It may be calculated by the number of true positive test results divided by the total number of positive test results.

In various examples, the model, classifier, or predictive test has a positive predictive value, of at least 40%, at least 45%, at least 50%, at least 55%, at least 60%, at least 65%, at least 70%, at least 75%, at least 80%, at least 85%, at least 90%, at least 95%, or at least 99%.

Negative predictive value, as used herein, generally refers to "the probability of a negative test result being correct". It may be calculated by the number of true negative test results divided by the total number of negative test results.

In various examples, the model, classifier, or predictive test has a negative predictive value, of at least 40%, at least 45%, at least 50%, at least 55%, at least 60%, at least 65%, at least 70%, at least 75%, at least 80%, at least 85%, at least 90%, at least 95%, or at least 99%.

C. Digital Processing Device

In some examples, the subject matter described herein can include a digital processing device or use of the same. In some examples, the digital processing device can include one or more hardware central processing units (CPU), graphics processing units (GPU), or tensor processing units (TPU) that perform the device's functions. In some examples, the digital processing device can include an operating system configured to perform executable instructions.

In some examples, the digital processing device can optionally be connected a computer network. In some examples, the digital processing device may be optionally connected to the Internet. In some examples, the digital processing device may be optionally connected to a cloud computing infrastructure. In some examples, the digital processing device may be optionally connected to an intranet. In some examples, the digital processing device may be optionally connected to a data storage device.

Non-limiting examples of suitable digital processing devices include server computers, desktop computers, laptop computers, notebook computers, sub-notebook computers, netbook computers, netpad computers, set-top computers, handheld computers, Internet appliances, mobile smartphones, and tablet computers. Suitable tablet computers can include, for example, those with booklet, slate, and convertible configurations.

In some examples, the digital processing device can include an operating system configured to perform executable instructions. For example, the operating system can include software, including programs and data, which manages the device's hardware and provides services for execution of applications. Non-limiting examples of operating systems include Ubuntu, FreeBSD, OpenBSD, NetBSD®, Linux, Apple® Mac OS X Server®, Oracle® Solaris®, Windows Server®, and Novell® NetWare®. Non-limiting examples of suitable personal computer operating systems include Microsoft® Windows®, Apple® Mac OS X®, UNIX®, and UNIX-like operating systems such as GNU/Linux®. In some examples, the operating system may be provided by cloud computing, and cloud computing resources may be provided by one or more service providers.

In some examples, the device can include a storage and/or memory device. The storage and/or memory device may be one or more physical apparatuses used to store data or programs on a temporary or permanent basis. In some examples, the device may be volatile memory and require power to maintain stored information. In some examples, the device may be non-volatile memory and retain stored information when the digital processing device is not powered. In some examples, the non-volatile memory can include flash memory. In some examples, the non-volatile memory can include dynamic random-access memory (DRAM). In some examples, the non-volatile memory can include ferroelectric random access memory (FRAM). In some examples, the non-volatile memory can include phase-change random access memory (PRAM).

In some examples, the device may be a storage device including, for example, CD-ROMs, DVDs, flash memory devices, magnetic disk drives, magnetic tapes drives, optical disk drives, and cloud computing-based storage. In some examples, the storage and/or memory device may be a combination of devices such as those disclosed herein. In some examples, the digital processing device can include a display to send visual information to a user. In some examples, the display may be a cathode ray tube (CRT). In some examples, the display may be a liquid crystal display (LCD). In some examples, the display may be a thin film transistor liquid crystal display (TFT-LCD). In some examples, the display may be an organic light emitting diode (OLED) display. In some examples, on OLED display may be a passive-matrix OLED (PMOLED) or active-matrix OLED (AMOLED) display. In some examples, the display may be a plasma display. In some examples, the display may be a video projector. In some examples, the display may be a combination of devices such as those disclosed herein.

In some examples, the digital processing device can include an input device to receive information from a user. In some examples, the input device may be a keyboard. In some examples, the input device may be a pointing device including, for example, a mouse, trackball, track pad, joystick, game controller, or stylus. In some examples, the input device may be a touch screen or a multi-touch screen. In some examples, the input device may be a microphone to capture voice or other sound input. In some examples, the input device may be a video camera to capture motion or visual input. In some examples, the input device may be a combination of devices such as those disclosed herein.

D. Non-Transitory Computer-Readable Storage Medium

In some examples, the subject matter disclosed herein can include one or more non-transitory computer-readable storage media encoded with a program including instructions executable by the operating system of an optionally networked digital processing device. In some examples, a computer-readable storage medium may be a tangible component of a digital processing device. In some examples, a computer-readable storage medium may be optionally removable from a digital processing device. In some examples, a computer-readable storage medium can include, for example, CD-ROMs, DVDs, flash memory devices, solid state memory, magnetic disk drives, magnetic tape drives, optical disk drives, cloud computing systems and services, and the like. In some examples, the program and instructions may be permanently, substantially permanently, semi-permanently, or non-transitorily encoded on the media.

E. Computer Systems

The present disclosure provides computer systems that are programmed to implement methods described herein. FIG. 1 shows a computer system 101 that is programmed or otherwise configured to store, process, identify, or interpret patient data, biological data, biological sequences, and reference sequences. The computer system 101 can process various aspects of patient data, biological data, biological sequences, or reference sequences of the present disclosure. The computer system 101 may be an electronic device of a user or a computer system that is remotely located with respect to the electronic device. The electronic device may be a mobile electronic device.

The computer system 101 comprises a central processing unit (CPU, also "processor" and "computer processor" herein) 105, which may be a single core or multi core processor, or a plurality of processors for parallel processing. The computer system 101 also comprises memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 may be a data storage unit (or data repository) for storing data. The computer system 101 may be operatively coupled to a computer network ("network") 130 with the aid of the communication interface 120. The network 130 may be the Internet, an internet and/or extranet, or an intranet and/or extranet that is in communication with the Internet. The network 130 in some examples is a telecommunication and/or data network. The network 130 can include one or more computer servers, which can enable distributed computing, such as cloud computing. The network 130, in some examples with the aid of the computer system 101, can implement a peer-to-peer network, which may enable devices coupled to the computer system 101 to behave as a client or a server.

The CPU 105 can execute a sequence of machine-readable instructions, which may be embodied in a program or software. The instructions may be stored in a memory location, such as the memory 110. The instructions may be directed to the CPU 105, which can subsequently program or otherwise configure the CPU 105 to implement methods of the present disclosure. Examples of operations performed by the CPU 105 can include fetch, decode, execute, and writeback.

The CPU 105 may be part of a circuit, such as an integrated circuit. One or more other components of the system 101 may be included in the circuit. In some examples, the circuit is an application specific integrated circuit (ASIC).

The storage unit 115 can store files, such as drivers, libraries and saved programs. The storage unit 115 can store user data, e.g., user preferences and user programs. The computer system 101 in some examples can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 101 via the network 130.

Methods as described herein may be implemented by way of machine (e.g., computer processor) executable code stored on an electronic storage location of the computer system 101, such as, for example, on the memory 110 or electronic storage unit 115. The machine-executable or machine-readable code may be provided in the form of software. During use, the code may be executed by the processor 105. In some examples, the code may be retrieved from the storage unit 115 and stored on the memory 110 for ready access by the processor 105. In some examples, the electronic storage unit 115 may be precluded, and machine-executable instructions are stored on memory 110.

The code may be pre-compiled and configured for use with a machine having a processer adapted to execute the code or may be interpreted or compiled during runtime. The code may be supplied in a programming language that may be selected to enable the code to execute in a pre-compiled, interpreted, or as-compiled fashion.

Aspects of the systems and methods provided herein, such as the computer system 101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements comprises optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, a nucleic acid sequence, an enriched nucleic acid sample, a methylation profile, an expression profile, and an analysis of a methylation or expression profile. Examples of UI's include, without limitation, a graphical user interface (GUI) and web-based user interface.

Methods and systems of the present disclosure may be implemented by way of one or more algorithms. An algorithm may be implemented by way of software upon execution by the central processing unit 105. The algorithm can, for example, store, process, identify, or interpret patient data, biological data, biological sequences, and reference sequences.

While certain examples of methods and systems have been shown and described herein, one of skill in the art will realize that these are provided by way of example only and not intended to be limiting within the specification. Numerous variations, changes, and substitutions will now occur to those skilled in the art without departing from the scope described herein. Furthermore, it shall be understood that all aspects of the described methods and systems are not limited to the specific depictions, configurations or relative proportions set forth herein which depend upon a variety of conditions and variables and the description is intended to include such alternatives, modifications, variations or equivalents.

In some examples, the subject matter disclosed herein can include at least one computer program or use of the same. A computer program can a sequence of instructions, executable in the digital processing device's CPU, GPU, or TPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

The functionality of the computer-readable instructions may be combined or distributed as desired in various environments. In some examples, a computer program can include one sequence of instructions. In some examples, a computer program can include a plurality of sequences of instructions. In some examples, a computer program may be provided from one location. In some examples, a computer program may be provided from a plurality of locations. In some examples, a computer program can include one or more software modules. In some examples, a computer program can include, in part or in whole, one or more web applications, one or more mobile applications, one or more standalone applications, one or more web browser plug-ins, extensions, add-ins, or add-ons, or combinations thereof.

In some examples, the computer processing may be a method of statistics, mathematics, biology, or any combination thereof. In some examples, the computer processing method comprises a dimension reduction method including, for example, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, and neural network.

In some examples, the computer processing method is a supervised machine learning method including, for example, a regression, support vector machine, tree-based method, and network.

In some examples, the computer processing method is an unsupervised machine learning method including, for example, clustering, network, principal component analysis, and matrix factorization.

F. Databases

In some examples, the subject matter disclosed herein can include one or more databases, or use of the same to store patient data, biological data, biological sequences, or reference sequences. Reference sequences may be derived from a database. In view of the disclosure provided herein, many databases may be suitable for storage and retrieval of the sequence information. In some examples, suitable databases can include, for example, relational databases, non-relational databases, object-oriented databases, object databases, entity-relationship model databases, associative databases, and XML databases. In some examples, a database may be internet-based. In some examples, a database may be web-based. In some examples, a database may be cloud computing-based. In some examples, a database may be based on one or more local computer storage devices.

In an aspect, the present disclosure provides a non-transitory computer-readable medium comprising instructions that direct a processor to perform a method disclosed herein.

In an aspect, the present disclosure provides a computing device comprising the computer-readable medium.

In another aspect, the present disclosure provides a system for performing classifications of biological samples comprising: a) a receiver to receive a plurality of training samples, each of the plurality of training samples having a plurality of classes of molecules, wherein each of the plurality of training samples comprises one or more known labels, b) a feature module to identify a set of features corresponding to an assay that are operable to be input to the machine learning model for each of the plurality of training samples, wherein the set of features correspond to properties of molecules in the plurality of training samples, wherein for each of the plurality of training samples, the system is operable to subject a plurality of classes of molecules in the training sample to a plurality of different assays to obtain sets of measured values, wherein each set of measured values is from one assay applied to a class of molecules in the training sample, wherein a plurality of sets of measured values are obtained for the plurality of training samples, c) an analysis module to analyze the sets of measured values to obtain a training vector for the training sample, wherein the training vector comprises feature values of the N set of features of the corresponding assay, each feature value corresponding to a feature and including one or more measured values, wherein the training vector is formed using at least one feature from at least two of the N sets of features corresponding to a first subset of the plurality of different assays, d) a labeling module to inform the system on the training vectors using parameters of the machine learning model to obtain output labels for the plurality of training samples, e) a comparator module to compare the output labels to the known labels of the training samples, f) a training module to iteratively search for optimal values of the parameters as part of training the machine learning model based on the comparing the output labels to the known labels of the training samples, and g) an output module to provide the parameters of the machine learning model and the set of features for the machine learning model.

VI. Methods of Classifying Subjects in a Population

The disclosed methods are directed to ascertaining genetic and/or epigenetic parameters of genomic DNA associated with colon cell proliferative disorders via analysis of cfDNA in a subject. The method is for use in the improved diagnosis, treatment and monitoring of colon cell proliferative disorders, more specifically by enabling the improved identification of and differentiation between stages or subclasses of said disorder and the genetic predisposition to said disorders.

In some embodiments, the method comprises analyzing the methylation status of CpG islands, CpG shores, or CpG shelves.

In some embodiments, the method comprises analyzing the methylation state, hemimethylation status, hypermethylation state, or hypomethylation state of a cell-free nucleic acid in a biological sample.

In an aspect, the present disclosure provides a method for detecting a colon cell proliferative disorder that may be applied to cell-free samples, e.g., to detect cell-free circulating colon cell proliferative disorder DNA. The method utilizes detection of methylation signals within a single sequencing read as the basic "positive" colon cell proliferative disorder signal.

In some embodiments, the colon cell proliferative disorder is selected from the group consisting of adenoma (adenomatous polyps), sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. In some embodiments, the colon cell proliferative disorder comprises the colorectal cancer.

In an aspect, the present disclosure provides a method for detecting a colon cell proliferative disorder, comprising: extracting DNA from a cell-free sample obtained from a subject, converting at least a portion of the DNA for methyl sequencing, amplifying regions methylated in cancer from the converted DNA, generating sequencing reads from the amplified regions, and detecting colon cell proliferative disorder signals comprising at least one, at least two, at least three, or more than three methylated regions within a cancer panel, to obtain input features that are inputted into a machine learning model to obtain a classifier capable of discriminating between two groups of subjects (e.g., healthy vs cancer, disease stage, advanced adenoma vs cancer).

The trained machine learning methods, models, and discriminate classifiers described herein may be applied toward various medical applications including cancer detection, diagnosis and treatment responsiveness. As models may be trained with individual metadata and analyte-derived features, the applications may be tailored to stratify individuals in a population and guide treatment decisions accordingly.

Diagnosis

Methods and systems provided herein may perform predictive analytics using artificial intelligence-based approaches to analyze acquired data from a subject (patient) to generate an output of diagnosis of the subject having a cancer (e.g., colorectal cancer). For example, the application may apply a prediction algorithm to the acquired data to generate the diagnosis of the subject having the cancer. The prediction algorithm may comprise an artificial intelligence-based predictor, such as a machine learning-based predictor, configured to process the acquired data to generate the diagnosis of the subject having the cancer.

The machine learning predictor may be trained using datasets, e.g., datasets generated by performing methylation assays using the signature panels described herein on biological samples of individuals from one or more sets of cohorts of patients having cancer as inputs and known diagnosis (e.g., staging and/or tumor fraction) outcomes of the subjects as outputs to the machine learning predictor.

Training datasets (e.g., datasets generated by performing methylation assays using the signature panels described herein on biological samples of individuals) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of cfDNA assay measurements, such as counts of cfDNA fragments in a biological sample obtained from a healthy and disease samples that overlap or fall within each of a set of bins (genomic windows) of a reference genome. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis (e.g., staging and/or tumor fraction) outcomes of the subject. Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of patients having or not having one or more cancers). Alternatively, training sets (e.g., training datasets) may be selected by proportionate sampling of a set of data corresponding to one or more sets of subjects (e.g., retrospective and/or prospective cohorts of patients having or not having one or more cancers). Training sets may be balanced across sets of data corresponding to one or more sets of subjects (e.g., patients from different clinical sites or trials). The machine learning predictor may be trained until certain pre-determined conditions for accuracy or performance are satisfied, such as having minimum desired values corresponding to diagnostic accuracy measures. For example, the diagnostic accuracy measure may correspond to prediction of a diagnosis, staging, or tumor fraction of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer (e.g., colorectal cancer).

In an aspect, the disclosure provides a method of using a classifier capable of distinguishing a population of individuals comprising: a) assaying a plurality of classes of molecules in the biological sample, wherein the assaying provides a plurality of sets of measured values representative of the plurality of classes of molecules; b) identifying a set of features corresponding to properties of each of the plurality of classes of molecules to be input to a machine learning or statistical model; c) preparing a feature vector of feature values from each of the plurality of sets of measured values, each feature value corresponding to a feature of the set of features and including one or more measured values, wherein the feature vector comprises at least one feature value obtained using each set of the plurality of sets of measured values; d) loading, into a memory of a computer system, a trained machine learning model comprising the classifier, the trained machine learning model trained using training vectors obtained from training biological samples, a first subset of the training biological samples identified as having a specified property and a second subset of the training biological samples identified as not having the specified property; and e) applying the trained machine learning model to the feature vector to obtain an output classification of whether the biological sample has the specified property, thereby distinguishing a population of individuals having the specified property.

In an aspect, the disclosure provides a method of using a hierarchy capable of distinguishing a population of individuals comprising: a) assaying a plurality of classes of molecules in the biological sample, wherein the assaying provides a plurality of sets of measured values representative of the plurality of classes of molecules; b) identifying a set of features corresponding to properties of each of the plurality of classes of molecules to be input to a machine learning or statistical model; c) preparing a feature vector of feature values from each of the plurality of sets of measured values, each feature value corresponding to a feature of the set of features and including one or more measured values, wherein the feature vector comprises at least one feature value obtained using each set of the plurality of sets of measured values; d) loading, into a memory of a computer system, a trained machine learning model comprising the classifier, the trained machine learning model trained using training vectors obtained from training biological samples, a first subset of the training biological samples identified as having a specified property and a second subset of the training biological samples identified as not having the specified property; and e) applying the trained machine learning model to the feature vector to obtain an output classification of whether the biological sample has the specified property, thereby distinguishing a population of individuals having the specified property.

In an aspect, the disclosure provides a method of using a hierarchy capable of distinguishing a population of individuals comprising: a) detecting of methylation signals within a single sequencing read of a pre-selected genomic region in one or more first patient samples, b) the methylation signals affect a hierarchy of data outputs to affect a machine learning model and c) a second patient sample using the affected hierarchy to detect methylation signals.

In some embodiments, the pre-selected genomic regions are selected from two or more methylated genomic regions in Tables 1-11, three or more methylated genomic regions in Tables 1-11, four or more methylated genomic regions in Tables 1-11, five or more methylated genomic regions in Tables 1-11, six or more methylated genomic regions in Tables 1-11, seven or more methylated genomic regions in Tables 1-11, eight or more methylated genomic regions in Tables 1-11, nine or more methylated genomic regions in Tables 1-11, ten or more methylated genomic regions in Tables 1-11, eleven or more methylated genomic regions in Tables 1-11, twelve or more methylated genomic regions in Tables 1-11, or thirteen or more methylated genomic regions in Tables 1-11.

In another aspect, the present disclosure provides a method for identifying a cancer in a subject, comprising: a) providing a biological sample comprising cell-free nucleic acid (cfNA) molecules from said subject; b) methyl converting and sequencing said cfNA molecules from said subject to generate a plurality of cfNA sequencing reads; c) aligning said plurality of cfNA sequencing reads to a reference genome; d) generating a quantitative measure of said plurality of cfNA sequencing reads at each of a first plurality of genomic regions of said reference genome to generate a first cfNA feature set, wherein said first plurality of genomic regions of said reference genome comprises at least about 10 distinct regions, each of said at least about 10 distinct regions comprising at least a portion of a gene selected from the group consisting of methylated regions in the signature panels described herein; and e) applying a trained algorithm to said first cfNA feature set to generate a likelihood of said subject having said cancer.

In some examples, said at least about 10 distinct regions comprises at least about 20 distinct regions, each of said at least about 20 distinct regions comprising at least a portion of a methylated region identified in Tables 1-11. In some examples, said at least about 10 distinct regions comprises at least about 30 distinct regions, each of said at least about 30 distinct regions comprising at least a portion of a methylated region identified in Tables 1-11.

As another example, such a pre-determined condition may be that the specificity of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a pre-determined condition may be that the positive predictive value (PPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a pre-determined condition may be that the negative predictive value (NPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a pre-determined condition may be that the area under the curve (AUC) of a Receiver Operating Characteristic (ROC) curve of predicting the colon cell proliferative disorder comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

Treatment Responsiveness

The predictive classifiers, systems, and methods described herein may be applied toward classifying populations of individuals for a number of clinical applications (e.g., based on performing methylation assays using the signature panels described herein on biological samples of individuals). Examples of such clinical applications include, detecting early-stage cancer, diagnosing cancer, classifying cancer to a particular stage of disease, determining responsiveness or resistance to a therapeutic agent for treating cancer.

The methods and systems described herein may be applied to characteristics of a colon cell proliferative disorder, such as grade and stage. Therefore, combinations of analytes and assays may be used in the present systems and methods to predict responsiveness of cancer therapeutics across different cancer types in different tissues and classifying individuals based on treatment responsiveness. In some embodiments, the classifiers described herein are capable of stratifying a group of individuals into treatment responders and non-responders.

The present disclosure also provides a method for determining a drug target of a condition or disease of interest (e.g., genes that are relevant or important for a particular class), comprising assessing a sample obtained from an individual for the level of gene expression for at least one gene; and using a neighborhood analysis routine, determining genes that are relevant for classification of the sample, to thereby ascertain one or more drug targets relevant to the classification.

The present disclosure also provides a method for determining the efficacy of a drug designed to treat a disease class, comprising obtaining a sample from an individual having the disease class; subjecting the sample to the drug; assessing the drug-exposed sample for the level of gene expression for at least one gene; and, using a computer model built with a weighted voting scheme, classifying the drug-exposed sample into a class of the disease as a function of relative gene expression level of the sample with respect to that of the model.

The present disclosure also provides a method for determining the efficacy of a drug designed to treat a disease class, wherein an individual has been subjected to the drug, comprising obtaining a sample from the individual subjected to the drug; assessing the sample for the level of gene expression for at least one gene; and using a model built with a weighted voting scheme, classifying the sample into a class of the disease including evaluating the gene expression level of the sample as compared to gene expression level of the model.

The present disclosure also provides a method of determining whether an individual belongs to a phenotypic class (e.g., intelligence, response to a treatment, length of life, likelihood of viral infection or obesity), comprising obtaining a sample from the individual; assessing the sample for the level of gene expression for at least one gene; and using a model built with a weighted voting scheme, classifying the sample into a class of the disease including evaluating the gene expression level of the sample as compared to gene expression level of the model.

In an aspect, the systems and methods described herein that relate to classifying a population based on treatment responsiveness refer to cancers that are treated with chemotherapeutic agents of the classes DNA damaging agents, DNA repair target therapies, inhibitors of DNA damage signaling, inhibitors of DNA damage induced cell cycle arrest and inhibition of processes indirectly leading to DNA damage, but not limited to these classes. Each of these chemotherapeutic agents may be considered a "DNA-damage therapeutic agent" as the term is used herein.

Based on a patient's analyte data, the patient may be classified into high-risk and low-risk patient groups, such as patient with a high or low risk of clinical relapse, and the results may be used to determine a course of treatment. For example, a patient determined to be a high-risk patient may be treated with adjuvant chemotherapy after surgery. For a patient deemed to be a low-risk patient, adjuvant chemotherapy may be withheld after surgery. Accordingly, the present disclosure provides, in certain aspects, a method for preparing a gene expression profile of a colon cancer tumor that is indicative of risk of recurrence.

In various examples, the classifiers described herein are capable of stratifying a population of individuals between responders and non-responders to treatment.

In another aspect, methods disclosed herein may be applied to clinical applications involving the detection or monitoring of cancer.

In some embodiments, methods disclosed herein may be applied to determine and/or predict response to treatment.

In some embodiments, methods disclosed herein may be applied to monitor and/or predict tumor load.

In some embodiments, methods disclosed herein may be applied to detect and/or predict residual tumor post-surgery.

In some embodiments, methods disclosed herein may be applied to detect and/or predict minimal residual disease post-treatment.

In some embodiments, methods disclosed herein may be applied to detect and/or predict relapse.

In an aspect, methods disclosed herein may be applied as a secondary screen.

In an aspect, methods disclosed herein may be applied as a primary screen.

In an aspect, methods disclosed herein may be applied to monitor cancer development.

In an aspect, methods disclosed herein may be applied to monitor and/or predict cancer risk.

VII. Identifying or Monitoring Colorectal Cancer

After using a trained algorithm to process the dataset, the colorectal cancer may be identified or monitored in the subject. The identification may be based at least in part on quantitative measures of sequence reads of the dataset at a panel of colorectal cancer-associated genomic loci (e.g., quantitative measures of RNA transcripts or DNA at the colorectal cancer-associated genomic loci).

The colorectal cancer may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the colorectal cancer by the trained algorithm may be calculated as the percentage of independent test samples (e.g., subjects known to have the colorectal cancer or subjects with negative clinical test results for the colorectal cancer) that are correctly identified or classified as having or not having the colorectal cancer.

The colorectal cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the colorectal cancer using the trained algorithm may be calculated as the percentage of cell-free biological samples identified or classified as having the colorectal cancer that correspond to subjects that truly have the colorectal cancer.

The colorectal cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the colorectal cancer using the trained algorithm may be calculated as the percentage of cell-free biological samples identified or classified as not having the colorectal cancer that correspond to subjects that truly do not have the colorectal cancer.

The colorectal cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the colorectal cancer using the trained algorithm may be calculated as the percentage of independent test samples associated with presence of the colorectal cancer (e.g., subjects known to have the colorectal cancer) that are correctly identified or classified as having the colorectal cancer.

The colorectal cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the colorectal cancer using the trained algorithm may be calculated as the percentage of independent test samples associated with absence of the colorectal cancer (e.g., subjects with negative clinical test results for the colorectal cancer) that are correctly identified or classified as not having the colorectal cancer.

In some embodiments, the trained algorithm may determine that the subject is at risk of colorectal cancer of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of colorectal cancer at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the colorectal cancer, the subject may be provided with a therapeutic intervention (e.g., prescribing or administering an appropriate course of treatment to treat the colorectal cancer of the subject). The therapeutic intervention may comprise a prescription of an effective dose of a drug, a further testing or evaluation of the colorectal cancer, a further monitoring of the colorectal cancer, or a combination thereof. If the subject is currently being treated for the colorectal cancer with a course of treatment, the therapeutic intervention may comprise a subsequent different course of treatment (e.g., to increase treatment efficacy due to non-efficacy of the current course of treatment). The therapeutic intervention may be described by, e.g., the "WHO list of priority medical devices for cancer management, WHO Medical device technical series", World Health Organization, ISBN: 978-92-4-156546-2, Geneva, 2017, the contents of which are incorporated herein by reference. The therapeutic intervention may be described by, for example, Wolpin et al., "Systemic Treatment of Colorectal Cancer," Gastroenterology, Vol. 134, Issue 5, 2008, pp. 1296-1310.e1, the contents of which are incorporated herein by reference.

The therapeutic intervention may comprise recommending the subject for a secondary clinical test to confirm a diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

The quantitative measures of sequence reads of the dataset at the panel of colorectal cancer-associated genomic loci (e.g., quantitative measures of RNA transcripts or DNA at the colorectal cancer-associated genomic loci) may be assessed over a duration of time to monitor a patient (e.g., subject who has colorectal cancer or who is being treated for colorectal cancer). In such cases, the quantitative measures of the dataset of the patient may change during the course of treatment. For example, the quantitative measures of the dataset of a patient with decreasing risk of the colorectal cancer due to an effective treatment may shift toward the profile or distribution of a healthy subject (e.g., a subject without colorectal cancer). Conversely, for example, the quantitative measures of the dataset of a patient with increasing risk of the colorectal cancer due to an ineffective treatment may shift toward the profile or distribution of a subject with higher risk of the colorectal cancer or a more advanced grade or stage of colorectal cancer.

The colorectal cancer of the subject may be monitored by monitoring a course of treatment for treating the colorectal cancer of the subject. The monitoring may comprise assessing the colorectal cancer of the subject at two or more time points. The assessing may be based at least on the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined at each of the two or more time points.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of one or more clinical indications, such as: (i) a diagnosis of the colorectal cancer of the subject; (ii) a prognosis of the colorectal cancer of the subject; (iii) an increased risk of the colorectal cancer of the subject; (iv) a decreased risk of the colorectal cancer of the subject; (v) an efficacy of the course of treatment for treating the colorectal cancer of the subject; and (vi) a non-efficacy of the course of treatment for treating the colorectal cancer of the subject.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of a diagnosis of the colorectal cancer of the subject. For example, if the colorectal cancer was not detected in the subject at an earlier time point but was detected in the subject at a later time point, then the difference is indicative of a diagnosis of the colorectal cancer of the subject. A clinical action or decision may be made based on this indication of diagnosis of the colorectal cancer of the subject, such as, for example, prescribing or administering a new therapeutic intervention for the subject. The clinical action or decision may comprise recommending the subject for a secondary clinical test to confirm the diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of a prognosis of the colorectal cancer of the subject.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of the subject having an increased risk of the colorectal cancer. For example, if the colorectal cancer was detected in the subject both at an earlier time point and at a later time point, and if the difference is a positive difference (e.g., the quantitative measures of sequence reads of the dataset at a panel of colorectal cancer-associated genomic loci (e.g., quantitative measures of RNA transcripts or DNA at the colorectal cancer-associated genomic loci) increased from the earlier time point to the later time point), then the difference may be indicative of the subject having an increased risk of the colorectal cancer. A clinical action or decision may be made based on this indication of the increased risk of the colorectal cancer, e.g., prescribing or administering a new therapeutic intervention or switching therapeutic interventions (e.g., ending a current treatment and prescribing or administering a new treatment) for the subject. The clinical action or decision may comprise recommending the subject for a secondary clinical test to confirm the increased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of the subject having a decreased risk of the colorectal cancer. For example, if the colorectal cancer was detected in the subject both at an earlier time point and at a later time point, and if the difference is a negative difference (e.g., the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci decreased from the earlier time point to the later time point), then the difference may be indicative of the subject having a decreased risk of the colorectal cancer. A clinical action or decision may be made based on this indication of the decreased risk of the colorectal cancer (e.g., continuing or ending a current therapeutic intervention) for the subject. The clinical action or decision may comprise recommending the subject for a secondary clinical test to confirm the decreased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of an efficacy of the course of treatment for treating the colorectal cancer of the subject. For example, if the colorectal cancer was detected in the subject at an earlier time point but was not detected in the subject at a later time point, then the difference may be indicative of an efficacy of the course of treatment for treating the colorectal cancer of the subject. A clinical action or decision may be made based on this indication of the efficacy of the course of treatment for treating the colorectal cancer of the subject, e.g., continuing or ending a current therapeutic intervention for the subject. The clinical action or decision may comprise recommending the subject for a secondary clinical test to confirm the efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

In some embodiments, a difference in the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci determined between the two or more time points may be indicative of a non-efficacy of the course of treatment for treating the colorectal cancer of the subject. For example, if the colorectal cancer was detected in the subject both at an earlier time point and at a later time point, and if the difference is a positive or zero difference (e.g., the quantitative measures of sequence reads of the dataset at a panel of colorectal cancer-associated genomic loci (e.g., quantitative measures of RNA transcripts or DNA at the colorectal cancer-associated genomic loci) comprising quantitative measures of a panel of colorectal cancer-associated genomic loci increased or remained at a constant level from the earlier time point to the later time point), and if an efficacious treatment was indicated at an earlier time point, then the difference may be indicative of a non-efficacy of the course of treatment for treating the colorectal cancer of the subject. A clinical action or decision may be made based on this indication of the non-efficacy of the course of treatment for treating the colorectal cancer of the subject, e.g., ending a current therapeutic intervention and/or switching to (e.g., prescribing or administering) a different new therapeutic intervention for the subject. The clinical action or decision may comprise recommending the subject for a secondary clinical test to confirm the non-efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a fecal immunochemical test (FIT), a fecal occult blood test (FOBT), or any combination thereof.

VIII. Kits

The present disclosure provides kits for identifying or monitoring a cancer of a subject. A kit may comprise probes for identifying a quantitative measure (e.g., indicative of a presence, absence, or relative amount) of sequences at each of a plurality of cancer-associated genomic loci in a cell-free biological sample of the subject. A quantitative measure (e.g., indicative of a presence, absence, or relative amount) of sequences at each of a plurality of cancer-associated genomic loci in the cell-free biological sample may be indicative of one or more cancers. The probes may be selective for the sequences at the plurality of cancer-associated genomic loci in the cell-free biological sample. A kit may comprise instructions for using the probes to process the cell-free biological sample to generate datasets indicative of a quantitative measure (e.g., indicative of a presence, absence, or relative amount) of sequences at each of the plurality of cancer-associated genomic loci in a cell-free biological sample of the subject.

The probes in the kit may be selective for the sequences at the plurality of cancer-associated genomic loci in the cell-free biological sample. The probes in the kit may be configured to selectively enrich nucleic acid (e.g., RNA or DNA) molecules corresponding to the plurality of cancer-associated genomic loci. The probes in the kit may be nucleic acid primers. The probes in the kit may have sequence complementarity with nucleic acid sequences from one or more of the plurality of cancer-associated genomic loci or genomic regions. The plurality of cancer-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more distinct cancer-associated genomic loci or genomic regions. The plurality of cancer-associated genomic loci or genomic regions may comprise one or more members selected from the group consisting of regions listed in Tables 1-11.

The instructions in the kit may comprise instructions to assay the cell-free biological sample using the probes that are selective for the sequences at the plurality of cancer-associated genomic loci in the cell-free biological sample. These probes may be nucleic acid molecules (e.g., RNA or DNA) having sequence complementarity with nucleic acid sequences (e.g., RNA or DNA) from one or more of the plurality of cancer-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the cell-free biological sample to generate datasets indicative of a quantitative measure (e.g., indicative of a presence, absence, or relative amount) of sequences at each of the plurality of cancer-associated genomic loci in the cell-free biological sample. A quantitative measure (e.g., indicative of a presence, absence, or relative amount) of sequences at each of a plurality of cancer-associated genomic loci in the cell-free biological sample may be indicative of one or more cancers.

The instructions in the kit may comprise instructions to measure and interpret assay readouts, which may be quantified at one or more of the plurality of cancer-associated genomic loci to generate the datasets indicative of a quantitative measure (e.g., indicative of a presence, absence, or relative amount) of sequences at each of the plurality of cancer-associated genomic loci in the cell-free biological sample. For example, quantification of array hybridization or polymerase chain reaction (PCR) corresponding to the plurality of cancer-associated genomic loci may generate the datasets indicative of a quantitative measure (e.g., indicative of a presence, absence, or relative amount) of sequences at each of the plurality of cancer-associated genomic loci in the cell-free biological sample. Assay readouts may comprise quantitative PCR (qPCR) values, digital PCR (dPCR) values, digital droplet PCR (ddPCR) values, fluorescence values, etc., or normalized values thereof.

EXAMPLES

Example 1: Selection of Methylated Regions for Colorectal Cancer Detection

For colorectal cancer, 20 regions in the genome were identified that are highly methylated in tumors but where multiple normal tissues do not exhibit methylation of these regions, using systems and methods of the present disclosure. These regions were used as highly specific markers for the presence of a tumor with little or no background signal.

In Table 12, 'position start-position end' designates the coordinates of the target regions in the hg18 build of the human genome reference sequence. The Gene ID and chromosome fields refer to the gene and chromosome number associated with the numbered region. Examination of these sequences relative to nearby genes indicates that they were found in upstream, in 5' promoters, in 5' enhancers, in introns, in exons, in distal promoters, in coding regions, or in intergenic regions.

Cell-free DNA was extracted from 250 microliter (μL) plasma (spiked with unique synthetic double-stranded DNA (dsDNA) fragments for sample tracking) using the Mag-MAX® Cell-Free DNA Isolation Kit (Applied Biosystems®), per manufacturer instructions. Paired-end sequencing libraries were prepared using the NEBNext® Ultra II DNA Library Prep Kit (New England Biolabs®), including polymerase chain reaction (PCR) amplification and unique molecular identifiers (UMIs), and sequenced using an Illumina® NovaSeq 6000 Sequencing System across multiple S2 or S4 flow cells at 2×5 1 base pairs to a minimum of 400 million reads (median=636 million reads).

Probes for Colorectal Cancer

PCR primer pairs were developed to the different regions in the genome shown to exhibit extensive methylation in multiple colorectal cancer samples from the TOGA database but with no or minimal methylation in multiple normal tissues and in blood cells (Peripheral Blood Mononuclear Cells and others).

These primers were then used to amplify converted DNA from plasma samples from individuals at risk of colorectal cancer. Sequencing adapters were ligated to the DNA and next-generation sequencing was performed. The sequencing reads were then separated by region and the sequence reads are analyzed using tools such as the BiQ Analyzer HT program.

Obtained sequencing reads were de-multiplexed, adapter trimmed, and aligned to a human reference genome (GRCh38 with decoys, alt contigs, and HLA contigs) using a Burrows Wheeler aligner (BWA-MEM 0.7.15). PCR duplicate fragments were removed using fragment endpoints and/or UMIs when present.

A cfDNA "profile" was created for each sample by counting the number of fragments that aligned to each putative protein-coding region of the genome. This type of data representation shows epigenetic changes in the cfDNA by variable nucleosome protection causing observed changes in coverage and fragments having increased methylation compared to control.

A set of functional regions of the human genome, comprising putatively protein-coding gene regions (with the genomic coordinate range including both introns and exons), was annotated in the sequencing data. The annotations for the protein-encoding gene regions ("gene" regions) were obtained from the Comprehensive Human Expressed SequenceS (CHESS) project (v1.0).

Results were obtained as follows.

Table 12 provides a collection of genomic regions identified in cell-free nucleic acid samples as being hypermethylated in samples from individuals with colorectal cancer. For each region, an exemplary number of methylated CpG sites in the region was provided as a threshold used to distinguish between healthy individuals and individuals with CRC.

TABLE 12

| Methyl Region (Gene ID; chromosome: region start-position end) | # of CpGs representing CRC threshold |
|---|---|
| ITGA4; chr2: 181457004-181457950 | 9 |
| EMBP1; chr1: 121519076-121519744 | 10 |
| TMEM163; chr2: 134718243-134719428 | 9 |
| SFMBT2; chr10: 7408046-7408953 | 11 |

TABLE 12-continued

| Methyl Region (Gene ID; chromosome: region start-position end) | # of CpGs representing CRC threshold |
|---|---|
| ELMO1; chr7: 37448612-37449471 | 4 |
| ZNF543; chr19: 57320164-57320845 | 5 |
| SFMBT2; chr10: 7410025-7411008 | 9 |
| CHST10; chr2: 100417269-100417795 | 8 |
| ELMO1; chr7: 37447852-37448217 | 4 |
| CCNA1; chr13: 36431498-36432414 | 17 |
| BEND4; chr4: 42150707-42153216 | 18 |
| KRBA1; chr7: 149714695-149715338 | 10 |
| S1PR1; chr1: 101236505-101237190 | 5 |
| PPP1R16B; chr20: 38805341-38807221 | 9 |
| IKZF1; chr7: 50304053-50304944 | 11 |
| LONRF2; chr2: 100322082-100322599 | 16 |
| ZFP82; chr19: 36418330-36418931 | 10 |
| FLT3; chr13: 28099881-28100943 | 13 |
| FBN1; chr15: 48644595-48646444 | 14 |
| FLI1; chr11: 128693042-128694372 | 11 |

In the discussion here, reference to genes such as ITGA4, TMEM163, and SFMBT2, for example, may not be indicative of the genes in question per se, but rather to the associated methylated regions described in the signature panel.

In total, 50 regions were found to be hypermethylated in association with CRC. Not all regions were necessary to be included in a classification model in order to distinguish between healthy individuals and individuals with CRC. Thus, some regions appear to be generally indicative of the various types of cancers assessed. Other regions are methylated in subgroups of these, while others are specific for cancers. In the context of this assay and the types of cancers examined, certain regions may be described as being "specifically methylated in colorectal cancer" and carry a higher weight in the signature when the sample sequences were trained in a predictive model. These higher weighted methylated regions associated with CRC are used in specific models trained to discriminate populations of individuals between healthy and CRC.

Example 2: Building and Training a Classification Model for Differentiating Populations of Individuals with Colorectal Cancer Using systems and methods of the present disclosure, a machine learning classification model was built and trained using artificial intelligence-based approaches to analyze acquired cfDNA data from a subject (to generate an output of diagnosis of the subject having a colorectal cancer).

Prospective human plasma samples were acquired from 49 patients diagnosed with CRC. In addition, a set of 92 control samples was acquired from patients without a current cancer diagnosis (but potentially with other comorbidities or undiagnosed cancer). All samples were de-identified.

Each patient's age, gender, and cancer stage (when available) were obtained for each sample. Plasma samples collected from each patient were stored at −80° C. and thawed prior to use. A description of the study cohort is provided in Table 13, which shows the number of healthy and cancer samples used for CRC experiments (by stage, gender, and age).

TABLE 13

| CRC | | Cancer (n = 24) | Control (n = 114) |
|---|---|---|---|
| Gender | Female n, (%) | 8 (33%) | 50 (44%) |
| | Male n, (%) | 16 (67%) | 64 (66%) |

TABLE 13-continued

| CRC | | Cancer (n = 24) | Control (n = 114) |
|---|---|---|---|
| Stage | I | 9 | |
| | II | 6 | |
| | III | 4 | |
| | IV | 2 | |
| | Unknown | 3 | |
| Age | Median/IQR | Median age: 65.0 IQR: 55.25-70.25 | Median age: 63.0 IQR: 56.0-68.0 |

Samples were processed and sequenced according to methods described herein, in particular those described in Example 1. Methylated regions in Table 12 were targeted specifically to determine methylated CpG status between healthy individuals and those with colorectal cancer. For each of the regions listed in column 1 of Table 12, the threshold number of CpG sites shown in column 2 was used to define a methylated fragment for analysis. The remaining fragments were categorized as methylated if they had a number of CpG sites that was greater than the threshold; otherwise, the fragments were categorized as not methylated. These counts were aggregated across regions for each sample, in order to calculate a raw score per sample, given by the number of methylated fragments per sample that overlapped with the regions listed in Table 12. The raw scores for each sample were normalized to account for coverage differences in each of the samples. Each sample's raw score was multiplied by a sample-specific scaling factor, given by a sample's total divided by a pre-specified target coverage level. These normalized and scaled methylated rates were outputted as the score per sample. A threshold score was chosen based on desired specificity targets from the training set. The samples were categorized as positive or negative, based on whether their score exceeded this threshold. An ROC curve was generated by considering the ranks of samples with this score or considering a threshold.

The machine learning classification model was trained as described above, and parameters were chosen on an independent held-out set of samples. The machine learning classification model was applied to the samples described in Table 13. The healthy sample with the highest scaled hypermethylated fragment count was selected as the cutoff for classifying new samples as positive or negative. Using the ranks induced by the normalized hypermethylated fragment counts, the area under the ROC curve (AUC) was calculated based on the above training set. Sensitivity and specificity were calculated using the selected cutoff. Confidence intervals for sensitivity and specificity were calculated using Clopper-Pearson confidence intervals, and confidence intervals for AUC were calculated using the method described by Fay, M. and Malinovsky, Y., Statistics in Medicine 37 (27): 3991-4006 (2018), the contents of which are incorporated herein by reference.

Figure 2:
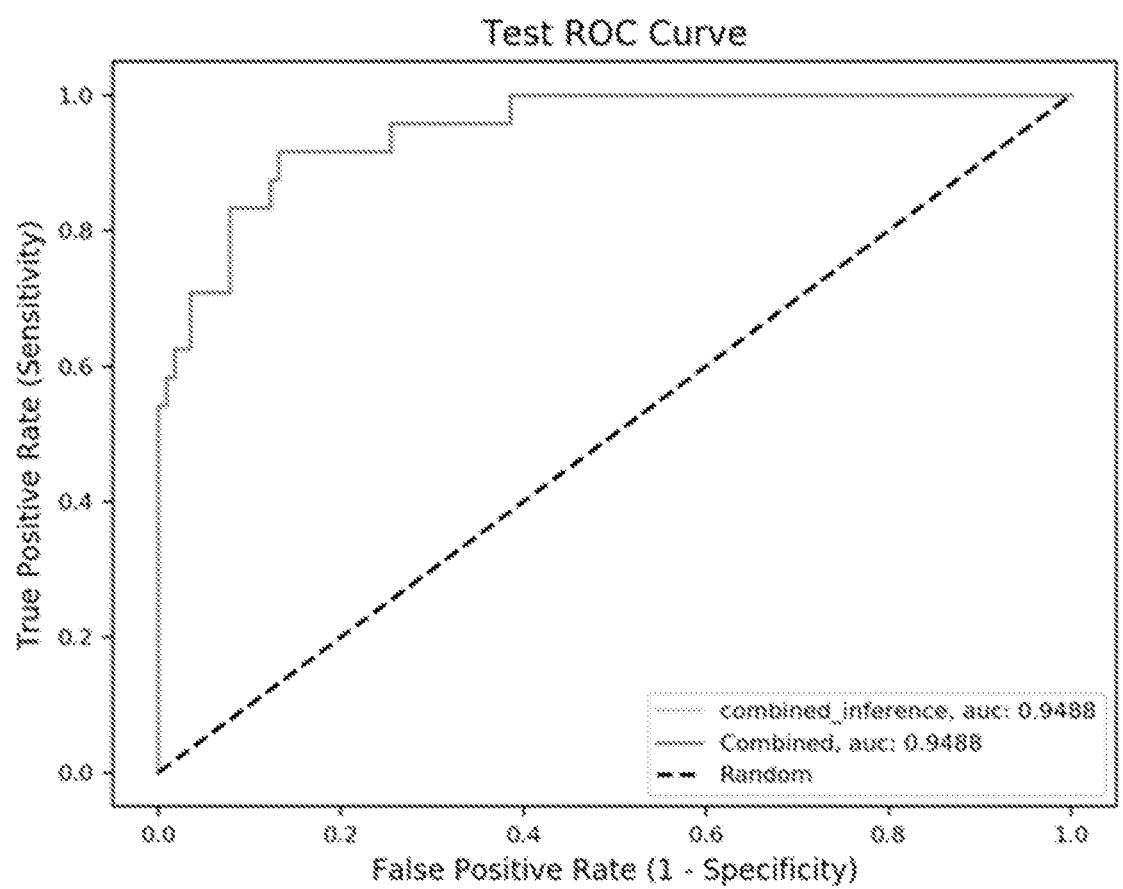
FIG. 2 provides an Area Under the Curve (AUC) curve for 4-fold cross validation of a model trained on the regions in Table 1.

This method achieved a mean area-under-the curve (AUC) of 0.9488 (0.87-0.98), with a mean sensitivity of 70% (0.49-0.87) at 92% % specificity (0.86-0.96) of IU samples (FIG. 2).

Example 3: Testing of Cell-Free Samples and Classification of Individuals

Using systems and methods of the present disclosure, predictive analytics was performed using artificial intelligence-based approaches to analyze acquired cfDNA data from a subject to generate an output of diagnosis of the subject having a colorectal cancer.

Provided herein is a method for predicting an increased risk of having or developing cancer, for an asymptomatic patient, wherein a model trained from the signature panel in process provided in Example 1 was applied to the measured panel of biomarkers, and the clinical factors of age and gender were used to identify those patients with an increased risk of having or developing colorectal cancer. In embodiments, this method and present classifier model used input variables of measured biomarkers that are within a normal clinical range, wherein the colorectal cancer classifier model classifies the patient in an increased risk category using input variables of age and the measured values of a panel of biomarkers from the patient when an output of the first classifier model is above a computational threshold based on number of methylated CpG sites in a region.

Genes were selected according to Example 1 with the aim of selecting marker genes and CpG sites with strong differential methylation (beta difference, e.g., the difference between the methylation specific probe and methylation non-specific probe, and p-value), predictive power (AUC), and an effect on gene expression (p-value from gene expression).

This selection yielded the signature panels provided herein, which contains methylated regions which can distinguish between healthy and CRC samples. The first subset of regions comprised 20 regions with increased methylation at least 4 to 18 CpG sites which map to 18 genes (many genes represented by many CpG sites).

A cfDNA CpG count-profile representation of the input cfDNA may serve as an unbiased representation of the available methylated signal in the blood allowing the capture of both signals directly from the tumor as well as those from non-tumor sources, such as the circulating immune system or tumor microenvironment.

Unsupervised clustering based on these genes showed clear patterns of methylation which correlates to healthy or CRC phenotypes.

Figure 3A:
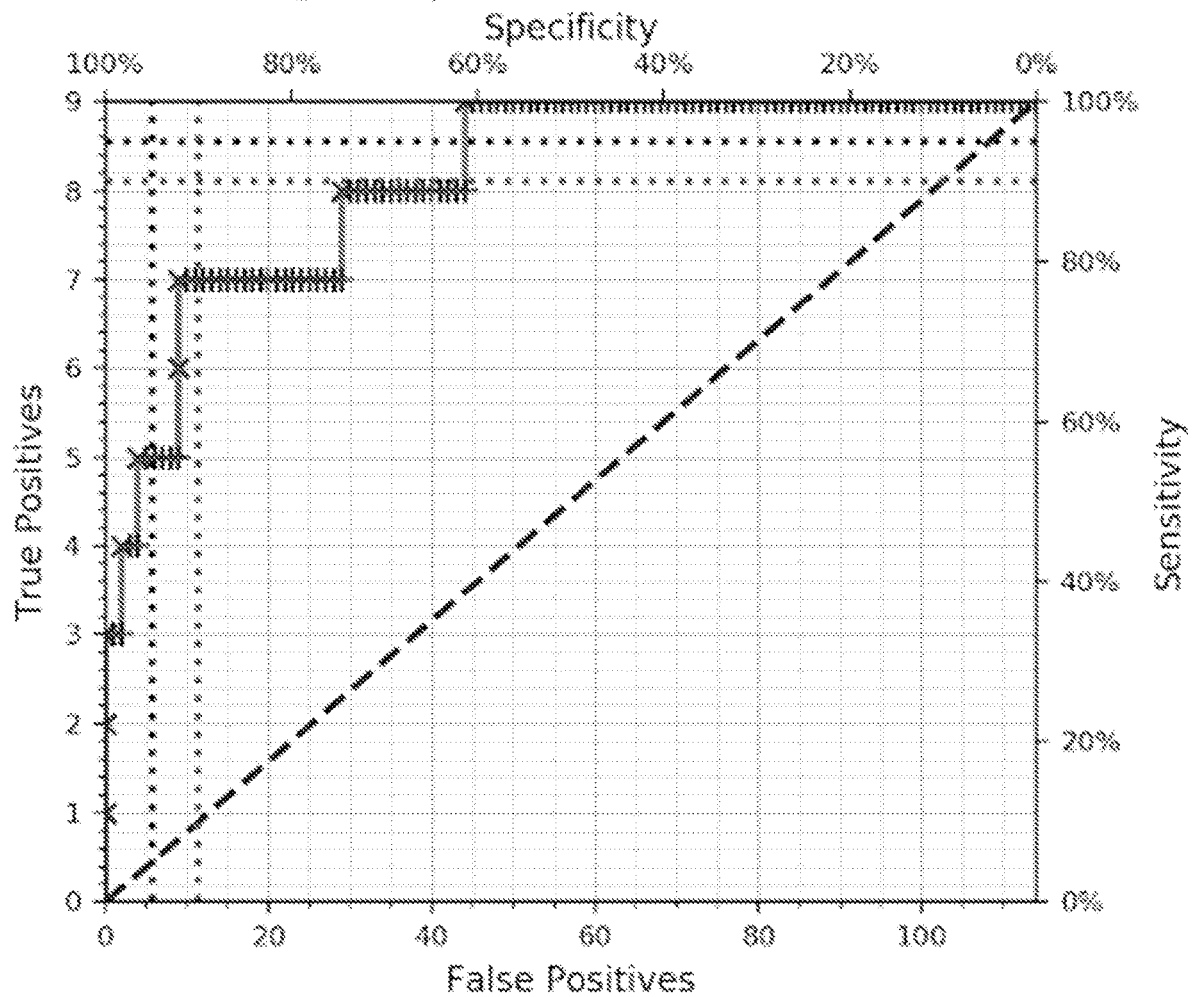
FIGS. 3A-3F provide a series of Area Under the Curve (AUC) curves for samples at various stages of CRC trained on a classification model.
Figure 3B:
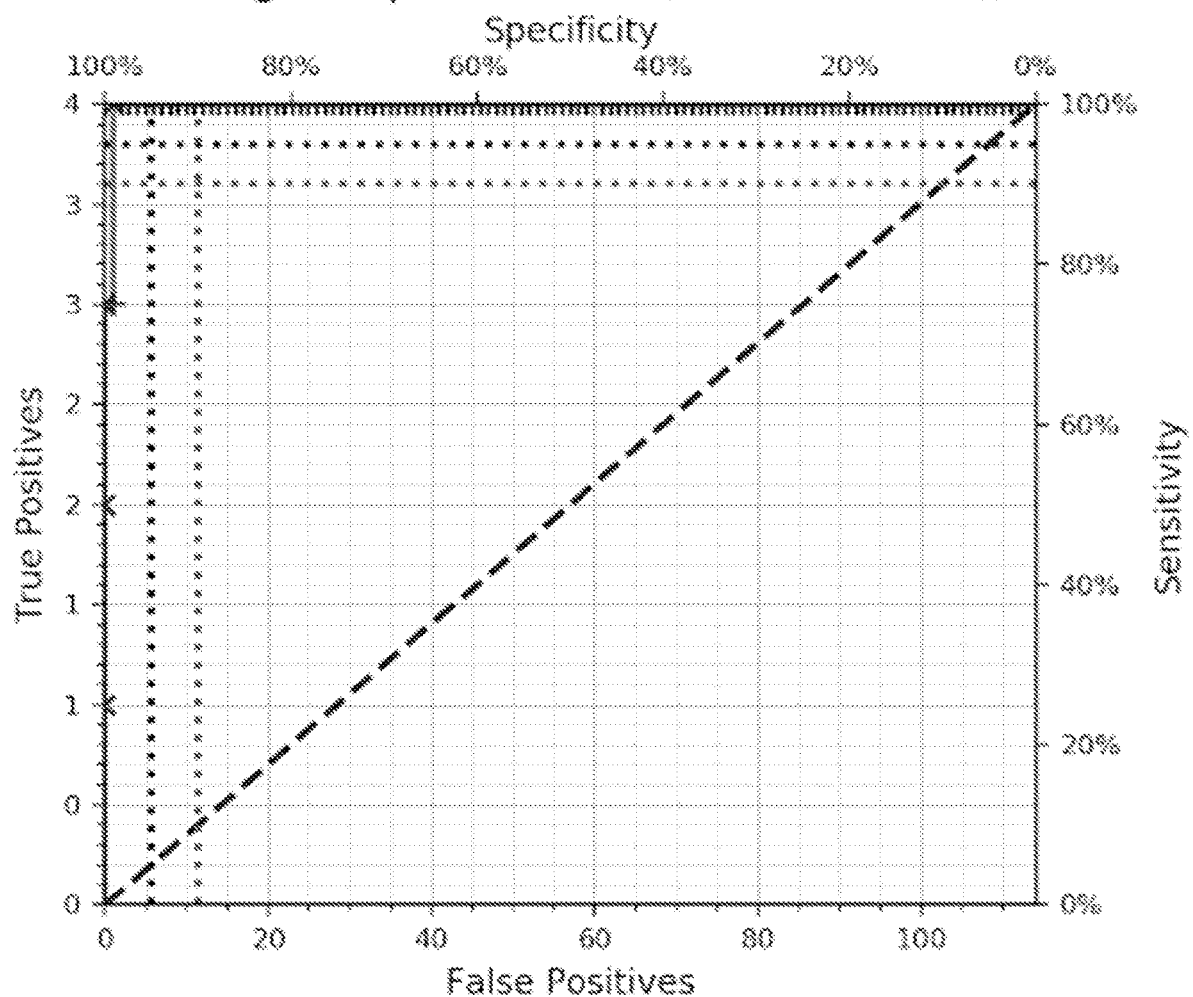
Figure 3C:
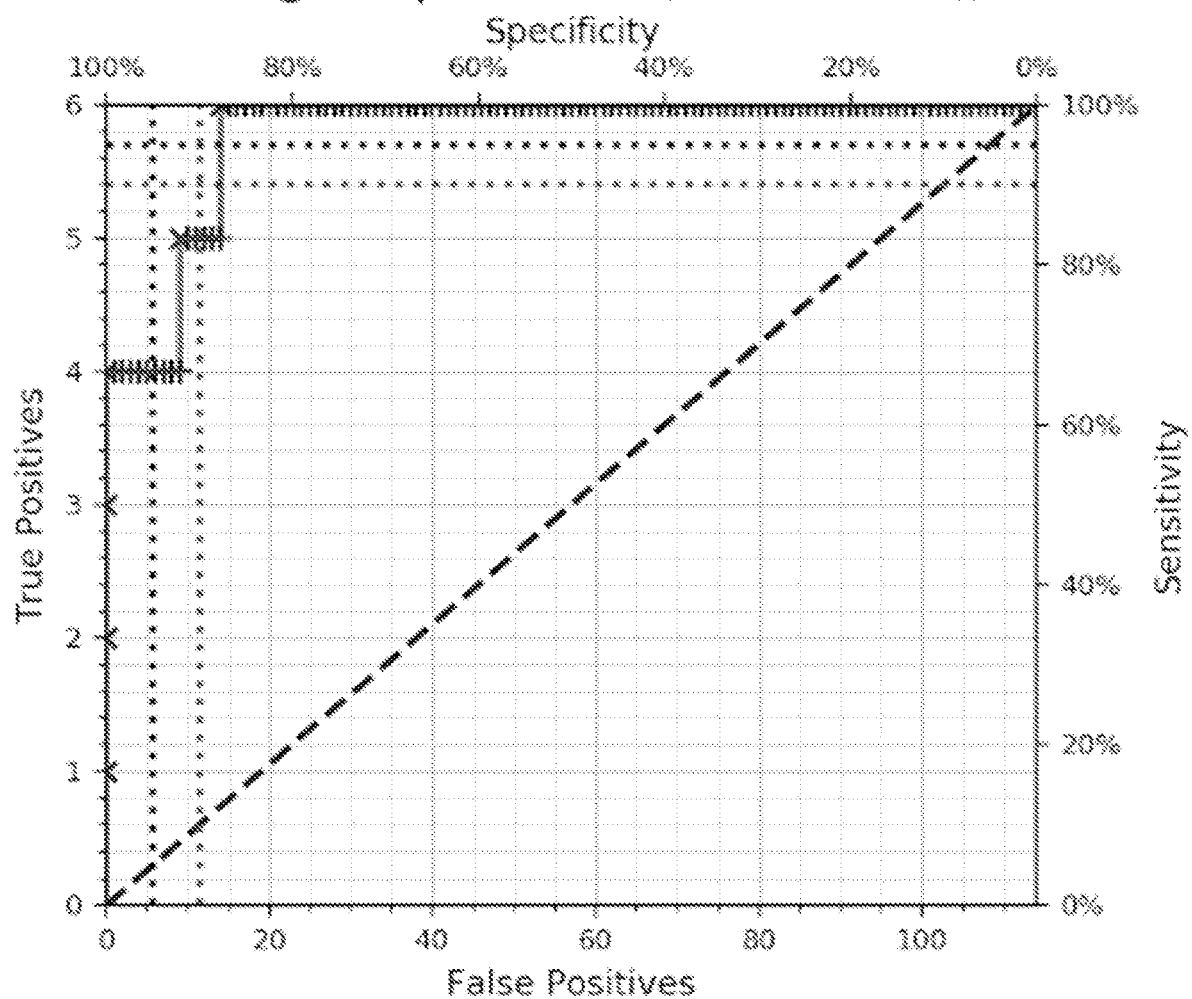
Figure 3D:
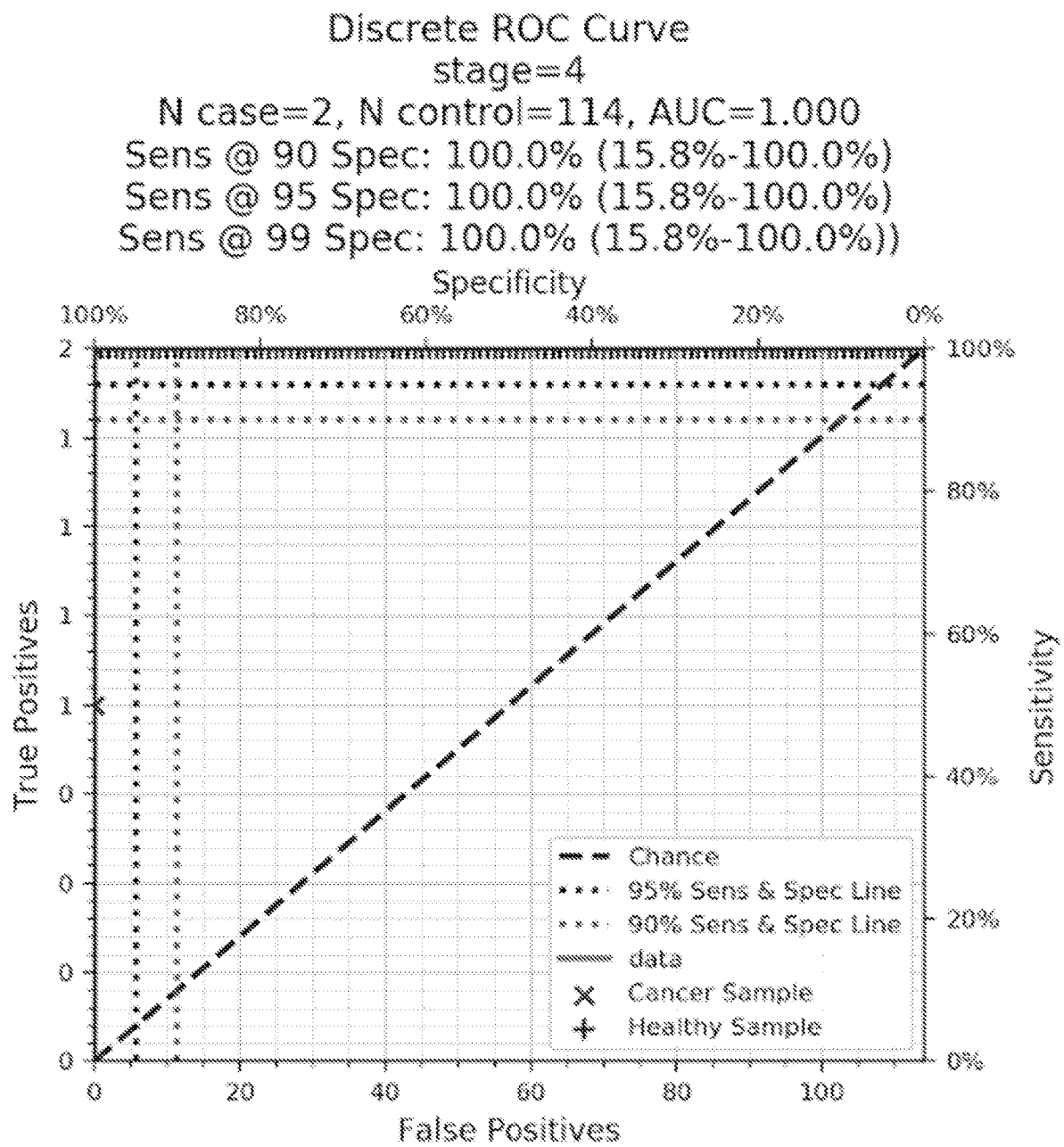
Figure 3E:
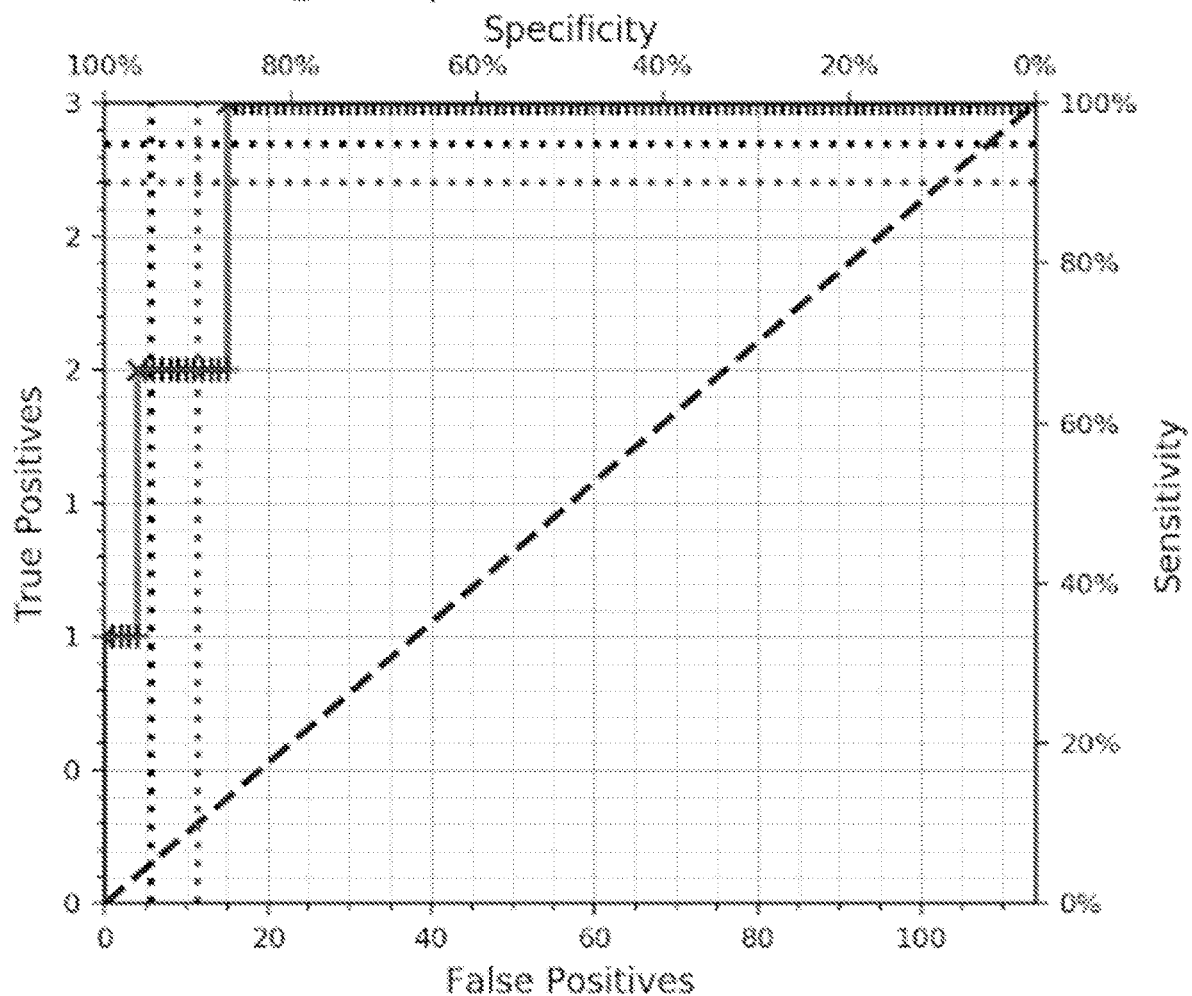
Figure 3F:
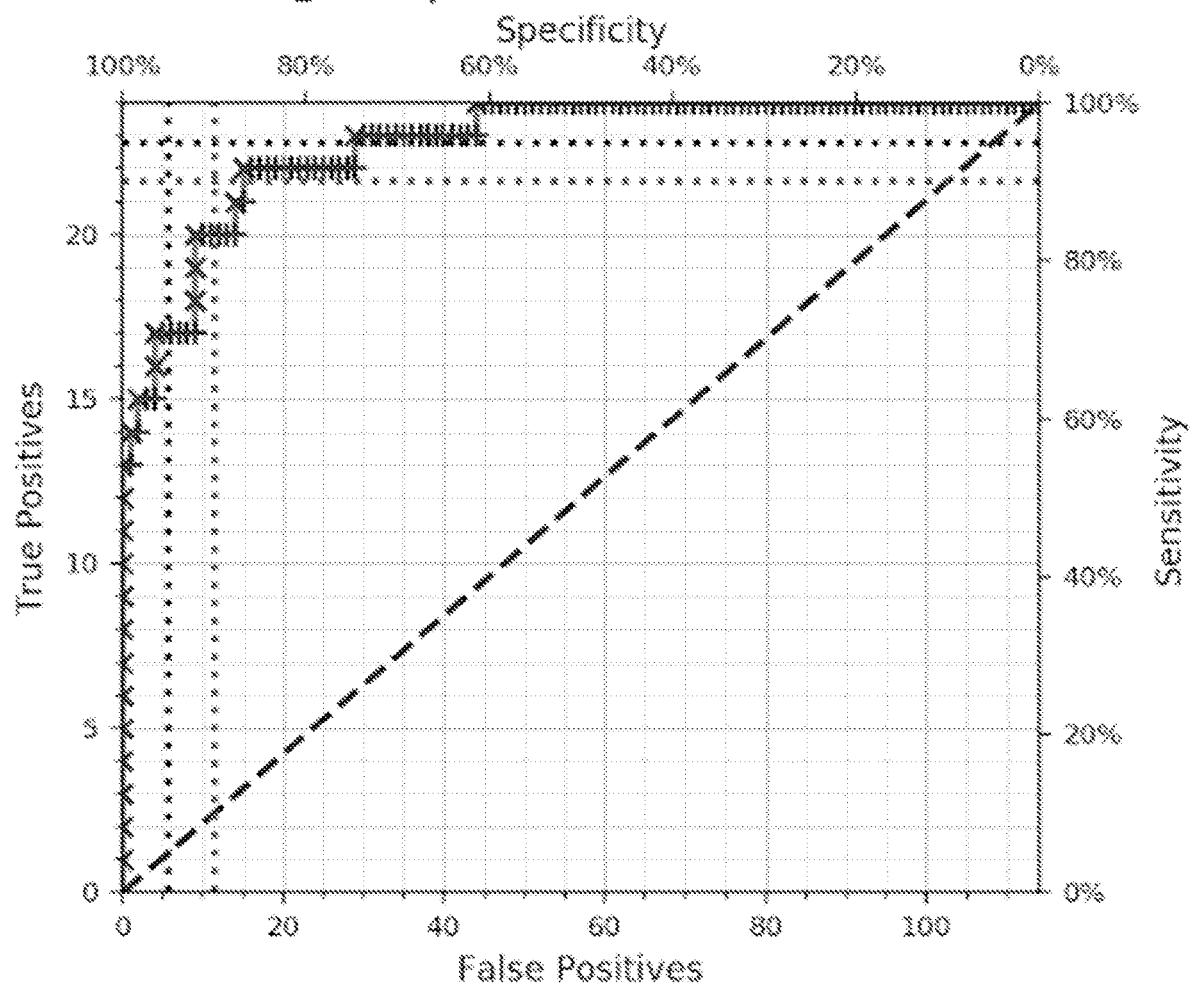

To evaluate the accuracy of methylated regions for early detection of CRC, receiver operating characteristic (ROC) curves and area under the ROC curves (AUCs) of the regions in the signature panel were calculated. FIGS. 3A-3F show the ROC results showing the ability of these differentially methylated regions (DMRs) to detect CRC and to differentiate early-stage cancer, including patients with stage 1 (FIG. 3A), stage 2 (FIG. 3B), stage 3 (FIG. 3C), stage 4 (FIG. 3D), missing stage (FIG. 3E), and all samples (FIG. 3F). Overall, 80 gene regions associated with increased methylation were identified. Methylated regions with mean methylation levels were increased progressively over the control, or may be used to differentiate CRC early-stage from late-stage. For example, methylated regions associated with Table 12 have a high ability to detect CRC [AUC of CRC vs. control=0.924 (95% CI: 0.752 to 0.954)].

As summarized in Table 14, the results demonstrated that early-stage cancer detection (e.g., among the set of 13 stage I and II samples) from the blood had excellent performance.

TABLE 14

|  | Sample size | AUC | Sensitivity at 90% Specificity | Sensitivity at 95% Specificity | Sensitivity at 99% Specificity |
| --- | --- | --- | --- | --- | --- |
| Stage = 1 | 9 | 0.905 | 77.8% | 55.6% | 33.3% |
| Stage = 2 | 4 | 0.998 | 100% | 100% | 100% |

TABLE 14-continued

|  | Sample size | AUC | Sensitivity at 90% Specificity | Sensitivity at 95% Specificity | Sensitivity at 99% Specificity |
| --- | --- | --- | --- | --- | --- |
| Stage = 3 | 6 | 0.966 | 83.3% | 66.7% | 66.7% |
| Stage = 4 | 2 | 1 | 100% | 100% | 100% |
| Unknown stage | 3 | 0.944 | 66.7% | 66.7% | 33.3% |
| All samples | 24 | 0.949 | 83.3% | 70.8% | 58.3% |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of treating a colorectal cancer in a subject, the method comprising:
   (a) subjecting a cell-free deoxyribonucleic acid (cfDNA) sample obtained or derived from the subject to conditions sufficient to convert unmethylated cytosines to uracils in nucleic acid molecules of the cfDNA sample, thereby generating a plurality of converted nucleic acid molecules;
   (b) contacting the plurality of converted nucleic acid molecules with nucleic acid probes complementary to a pre-determined methylation signature panel of at least two genomic regions selected from the group consisting of
   ITGA4, chr2: 181457004-181457950;
   EMBP1, chr1: 121519076-121519744;
   TMEM163, chr2: 134718243-134719428;
   SFMBT2, chr10: 7408046-7408953;
   ELMO1, chr7: 37448612-37449471;
   ZNF543, chr19: 57320164-57320845;
   SFMBT2, chr10: 7410025-7411008;
   CHST10, chr2: 100417269-100417795;
   ELMO1, chr7: 37447852-37448217;
   CCNA1, chr13: 36431498-36432414;
   BEND4, chr4: 42150707-42153216;
   KRBA1, chr7: 149714695-149715338;
   S1PR1, chr1: 101236505-101237190;
   PPP1R16B, chr20: 38805341-38807221;
   IKZF1, chr7: 50304053-50304994;
   LONRF2, chr2: 100322082-100322599;
   ZFP82, chr19: 36418330-36418931;

FLT3, chr13: 28099881-28100943;
FBN1, chr15: 48644595-48646444; and
FLI1, chr11: 128693042-128694372,
to enrich for sequences corresponding to the pre-determined methylation signature panel;
(c) determining a threshold value for each of the at least two genomic regions, wherein the threshold value is indicative of a number of methylated CpG sites in each of the at least two genomic regions;
(d) comparing the number of methylated CpG sites in each of the at least two genomic regions to the threshold value;
(e) determining that the number of methylated CpG sites in each of the at least two genomic regions is above the threshold value, thereby identifying the subject as having the colorectal cancer; and
(f) responsive to the determining in (e), administering a therapeutic intervention to the subject to treat the colorectal cancer in the subject, wherein the therapeutic intervention comprises a chemotherapy, a radiotherapy, an immunotherapy, or a surgery.

2. The method of claim 1, further comprising amplifying the plurality of converted, enriched nucleic acid molecules.

3. The method of claim 2, wherein the amplifying comprises polymerase chain reaction (PCR).

4. The method of claim 1, further comprising sequencing the plurality of converted, enriched nucleic acid molecules at a depth of greater than 1000×, thereby generating nucleic acid sequences.

5. The method of claim 4, further comprising aligning the nucleic acid sequences to a reference human genome, thereby generating a methylation profile of the subject, wherein the reference human genome is hg18 or hg19.

6. The method of claim 1, wherein the pre-determined methylation signature panel comprises three or more genomic regions selected from the group consisting of
ITGA4, chr2: 181457004-181457950;
EMBP1, chr1: 121519076-121519744;
TMEM163, chr2: 134718243-134719428;
SFMBT2, chr10: 7408046-7408953;
ELMO1, chr7: 37448612-37449471;
ZNF543, chr19: 57320164-57320845;
SFMBT2, chr10: 7410025-7411008;
CHST10, chr2: 100417269-100417795;
ELMO1, chr7: 37447852-37448217;
CCNA1, chr13: 36431498-36432414;
BEND4, chr4: 42150707-42153216;
KRBA1, chr7: 149714695-149715338;
S1PR1, chr1: 101236505-101237190;
PPP1R16B, chr20: 38805341-38807221;
IKZF1, chr7: 50304053-50304994;
LONRF2, chr2: 100322082-100322599;
ZFP82, chr19: 36418330-36418931;
FLT3, chr13: 28099881-28100943;
FBN1, chr15: 48644595-48646444; and
FLI1, chr11: 128693042-128694372.

7. The method of claim 1, wherein the pre-determined methylation signature panel comprises six or more genomic regions selected from the group consisting of
ITGA4, chr2: 181457004-181457950;
EMBP1, chr1: 121519076-121519744;
TMEM163, chr2: 134718243-134719428;
SFMBT2, chr10: 7408046-7408953;
ELMO1, chr7: 37448612-37449471;
ZNF543, chr19: 57320164-57320845;
SFMBT2, chr10: 7410025-7411008;
CHST10, chr2: 100417269-100417795;
ELMO1, chr7: 37447852-37448217;
CCNA1, chr13: 36431498-36432414;
BEND4, chr4: 42150707-42153216;
KRBA1, chr7: 149714695-149715338;
S1PR1, chr1: 101236505-101237190;
PPP1R16B, chr20: 38805341-38807221;
IKZF1, chr7: 50304053-50304994;
LONRF2, chr2: 100322082-100322599;
ZFP82, chr19: 36418330-36418931;
FLT3, chr13: 28099881-28100943;
FBN1, chr15: 48644595-48646444; and
FLI1, chr11: 128693042-128694372.

8. The method of claim 1, wherein the pre-determined methylation signature panel comprises nine or more genomic regions selected from the group consisting of
ITGA4, chr2: 181457004-181457950;
EMBP1, chr1: 121519076-121519744;
TMEM163, chr2: 134718243-134719428;
SFMBT2, chr10: 7408046-7408953;
ELMO1, chr7: 37448612-37449471;
ZNF543, chr19: 57320164-57320845;
SFMBT2, chr10: 7410025-7411008;
CHST10, chr2: 100417269-100417795;
ELMO1, chr7: 37447852-37448217;
CCNA1, chr13: 36431498-36432414;
BEND4, chr4: 42150707-42153216;
KRBA1, chr7: 149714695-149715338;
S1PR1, chr1: 101236505-101237190;
PPP1R16B, chr20: 38805341-38807221;
IKZF1, chr7: 50304053-50304994;
LONRF2, chr2: 100322082-100322599;
ZFP82, chr19: 36418330-36418931;
FLT3, chr13: 28099881-28100943;
FBN1, chr15: 48644595-48646444; and
FLI1, chr11: 128693042-128694372.

9. The method of claim 1, wherein the pre-determined methylation signature panel comprises twelve or more genomic regions selected from the group consisting of
ITGA4, chr2: 181457004-181457950;
EMBP1, chr1: 121519076-121519744;
TMEM163, chr2: 134718243-134719428;
SFMBT2, chr10: 7408046-7408953;
ELMO1, chr7: 37448612-37449471;
ZNF543, chr19: 57320164-57320845;
SFMBT2, chr10: 7410025-7411008;
CHST10, chr2: 100417269-100417795;
ELMO1, chr7: 37447852-37448217;
CCNA1, chr13: 36431498-36432414;
BEND4, chr4: 42150707-42153216;
KRBA1, chr7: 149714695-149715338;
S1PR1, chr1: 101236505-101237190;
PPP1R16B, chr20: 38805341-38807221;
IKZF1, chr7: 50304053-50304994;
LONRF2, chr2: 100322082-100322599;
ZFP82, chr19: 36418330-36418931;
FLT3, chr13: 28099881-28100943;
FBN1, chr15: 48644595-48646444; and
FLI1, chr11: 128693042-128694372.

10. The method of claim 1, wherein the colorectal cancer is selected from the group consisting of stage 1 colorectal cancer, stage 2 colorectal cancer, stage 3 colorectal cancer, and stage 4 colorectal cancer.

11. The method of claim 1, wherein the pre-determined methylation signature panel comprises a genomic region selected from the group consisting of:

IKZF1; chr: 50304053-50304944;
ELMO1; chr7: 37448612-37449471; and
ELMO; chr7: 37447852-37448217.

12. The method of claim 1, wherein the pre-determined methylation signature panel comprises a genomic region selected from the group consisting of:
IKZF1; chr: 50304053-50304944;
ELMO1; chr7: 37448612-37449471;
ELMO; chr7: 37447852-37448217; and
FLI1; chr11: 128693042-128694372.

13. The method of claim 1, further comprising performing a colonoscopy on the subject after (e) to treat the colorectal cancer.

* * * * *